(12) United States Patent
Surendranath et al.

(10) Patent No.: US 11,668,013 B2
(45) Date of Patent: Jun. 6, 2023

(54) CONTROLLED ELECTROCHEMICAL OXIDATION OF PT(II) IONS FOR CONTINUOUS METHANE-TO-METHANOL CONVERSION

(71) Applicant: Massachusetts Institute of Technology, Cambridge, MA (US)

(72) Inventors: Yogesh Surendranath, Cambridge, MA (US); R. Soyoung Kim, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 372 days.

(21) Appl. No.: 16/820,266

(22) Filed: Mar. 16, 2020

(65) Prior Publication Data

US 2020/0291535 A1 Sep. 17, 2020

Related U.S. Application Data

(60) Provisional application No. 62/819,046, filed on Mar. 15, 2019.

(51) Int. Cl.
*C25B 3/07* (2021.01)
*C25B 3/23* (2021.01)
(Continued)

(52) U.S. Cl.
CPC ............... *C25B 3/23* (2021.01); *B01J 27/13* (2013.01); *C25B 11/02* (2013.01); *C25B 11/04* (2013.01);
(Continued)

(58) Field of Classification Search
CPC ...... C25B 3/07; C25B 3/23; C25B 9/15; C25B 15/08; C25B 15/029
(Continued)

(56) References Cited

U.S. PATENT DOCUMENTS

| 4,120,759 A * | 10/1978 | Asami | C25D 21/12 205/82 |
|---|---|---|---|
| 2003/0024821 A1* | 2/2003 | Chopra | C25D 21/18 205/333 |
| 2016/0064743 A1* | 3/2016 | Lu | H01M 4/8652 423/437.1 |

FOREIGN PATENT DOCUMENTS

| WO | WO-2018/031893 A1 | 2/2018 | |
|---|---|---|---|
| WO | WO-2018031893 A1 * | 2/2018 | ............ C25B 11/04 |

OTHER PUBLICATIONS

Liu et al., "Electrocatalytic Shilov Chemistry for the Oxidation of Aliphatic Groups," Molecular Catalysis (Feb. 1, 2019), vol. 463, pp. 16-19. (Year: 2019).*
(Continued)

*Primary Examiner* — Edna Wong
(74) *Attorney, Agent, or Firm* — Foley Hoag LLP; Dana M. Gordon; Tatiana P. Headrick

(57) ABSTRACT

Disclosed is an electrochemical method for continuous regeneration of a $Pt^{IV}$ oxidant to furnish overall electrochemical methane oxidation. Cl-adsorbed Pt electrodes catalyze facile oxidation of $Pt^{II}$ to $Pt^{IV}$ without concomitant methanol oxidation. Exploiting this electrochemistry, the $Pt^{II/IV}$ ratio in solution is maintained via in situ monitoring of the solution potential coupled with dynamic modulation of the electric current. Remarkably, this method leads to sustained methane oxidation catalysis with ~70% selectivity for methanol.

19 Claims, 19 Drawing Sheets

(51) Int. Cl.

| | | |
|---|---|---|
| C25B 9/15 | (2021.01) | |
| C25B 15/08 | (2006.01) | |
| C25B 15/029 | (2021.01) | |
| C25B 11/04 | (2021.01) | |
| B01J 27/13 | (2006.01) | |
| C25B 11/02 | (2021.01) | |
| C25B 15/02 | (2021.01) | |
| C07C 31/04 | (2006.01) | |

(52) U.S. Cl.
CPC .............. *C25B 15/02* (2013.01); *C25B 15/08* (2013.01); *C07C 31/04* (2013.01)

(58) Field of Classification Search
USPC .................................................. 205/413, 452
See application file for complete search history.

(56) References Cited

OTHER PUBLICATIONS

Luinstra et al., "Mechanism and Stereochemistry for Nucleophilic Attack at Carbon of Platinum(IV) Alkyls: Model Reactions for Hydrocarbon Oxidation with Aqueous Platinum Chlorides," Journal of the American Chemical Society (Apr. 1993), vol. 115, No. 7, pp. 3004-3005. (Year: 1993).*
International Search Report and Written Opinion for International Application No. PCT/US20/22987 dated Jun. 11, 2020.
Ahlquist et al., "Product protection, the key to developing high performance methane selective oxidation catalysts," J Am Chem Soc, 131:17110-17115 (2009).
Ayres et al., "Spectrophotometric study of the platinum(IV)-Tin(II) chloride system," Analytical Chemistry, 299-304 (1951).
Balashova et al., "Study of the structure of the electrical double layer on the platinum by the radioactive tracer method," Russ Chem Rev, 34:730 (1965).
Bar-Nahum et al., "Mild, aqueous, aerobic, catalytic oxidation of methane to methanol and acetaldehyde catalyzed by a supported bipyrimidinylplatinum-polyoxometalate hybrid compound," J Am Chem Soc, 126:10236-10237 (2004).
Bratsch, "Standard electrode potentials and temperature coefficients in water at 298.15 K," J Phys Chem Ref Data, 18(1):1-21 (1969).
Cameron et al., "Multielectron-photoinduced reduction of chloroplatinum complexes: Visible light deposition of platinum metal," Inorganic Chemistry, 25(16):2910-2913 (1986).
Chung et al., "Methanol electro-oxidation on the Pt Surface: Revisiting the cyclic voltammetry interpretation," The Journal of Physical Chemistry C, 120:9028-9035 (2016).
Cox et al., "Photoaquation of hexachloroplatinate (IV)," J Inorg Nucl Chem, 34:297-305 (1972).
Cui et al., "Room-temperature methane conversion by graphene-confined single iron atoms," Chem, 4:1902-1910 (2018).
Cushing et al., "Study of the kinetics of electrochemical reactions by thin-layer voltammetry," J Electroanal Chem, 23:183-203 (1969).
Da Silva, "Synthesis of methanol from methane: Challenges and advances on the multi-step (syngas) and one-step routes (DMTM)," Fuel Processing Technology, 145:42-61 (2016).
DeVries et al., "Catalytic hydroxylation using chloroplatinum compounds," Journal of Molecular Catalysis A: Chemical, 189:17-22 (2002).
Elding et al., "Electronic absorption spectra of square-planar chloro-aqua and bromo-aqua complexes of palladium(II) and platinum(II)," The Journal of Physical Chemistry, 82(1):69-74 (1978).
Elding et al., "Kinetics and mechanism for chloride anation of some platinum(IV) aqua complexes in the presence of platinum(II)," Inorganica Chimica Acta, 19:31-38 (1976).
Elding et al., "The solvent path in square-planar substitutions. Kinetics and mechanism for reactions of tetrachloroplatinate(II) and aquachloroplatinates(II) with halides, thiocyanate, and dimethyl sulfoxide," Inorganica Chimica Acta, 31:243-250 (1978).
Elding, "Preparation and properties of the tetra-aquaplatinum(II) ion in perchloric acid solution," Inorganica Chimica Acta, 20:65-69 (1976).
Freund et al., "Electrocatalytic functionalization of alkanes using aqueous platinum salts," Journal of Molecular Catalysis, 87:L11-L15 (1994).
Goldshleger et al., "Pt(II) complexes in activation of saturated hydrocarbons," React Kinet Catal Lett, 6(1):43-50 (1977).
Gunsalus et al., "Homogeneous functionalization of methane," Chemical Reviews, 1-53 (2017).
Henglein et al., "Absorption spetrum and some chemical reactions of colloidal platinum in aqueous solution," J Phys Chem, 99:14129-14136 (1995).
Holmen, "Direct conversion of methane to fuels and chemicals," Catalysis Today, 142:2-8 (2009).
Horvath et al., "Low-temperature methane chlorination with aqueous platinum chlorides in the presence of chlorine," Organometallics, 12:8-10 (1993).
Jerkiewicz et al., "Surface-oxide growth at platinum electrodes in aqueous H2SO4 reexamination of its mechanism through combined cyclic-voltammetry, electrochemical quartz-crystal nanobalance, and Auger electron spectroscopy measurements," Electrochimica Acta, 49:1451-1459 (2004).
Jude et al., "An outer-sphere two-electron platinum reagent," J Am Chem Soc, 125:3446-3447 (2003).
Kent et al., "Water oxidation and oxygen monitoring by cobalt-modified fluorine-doped tin oxide electrodes," J Am Chem Soc, 135:8432-8435 (2013).
Kim et al., "Electrochemical reoxidation enables continuous methane-to-methanol catalysis with aqueous Pt salts," ACS Cent Sci, 1-8 (2019).
Kirkland et al., "Ultraviolet spectrophotometric determination of platinum," Analytica Chimica Acta, 9:441-446 (1953).
Kreutz et al., "Evolution of catalysts directed by genetic algorithms in a plug-based microfluidic device tested with oxidation of methane by oxygen," J Am Chem Soc, 132:3128-3132 (2010).
Labinger et al., "Mechanistic studies on the Shilov system: A retrospective," Journal of Organometallic Chemistry, 793:47-53 (2015).
Labinger, J. A. "Chapter 2. Alkane Functionalization via Electrophilic Activation," in "Catalysis by Metal Complexes: vol. 38, Alkane C—H Activation by Single-Site Metal Catalysis," Pérez, P. J., Ed.; Catalysis by Metal Complexes; Springer Netherlands: Dordrecht, 2012; vol. 38, pp. 17-71.
Latimer et al., "Direct methane to methanol: The selectivity—conversion limit and design strategies," ACS Catal, 8:6894-6907 (2018).
Lee et al., "Platinum-catalyzed, terminal-selective C(sp3)-H oxidation of aliphatic amines," J Am Chem Soc, 137:12796-12799 (2015).
Lin et al., "Catalytic Shilov chemistry: platinum chloride-catalyzed oxidation of terminal methyl groups by dioxygen," J Am Chem Soc, 123:1000-1001 (2001).
Liu et al., "Electrocatalytic Shilov chemistry for the oxidation of aliphatic groups," Molecular Catalysis, 463:16-19 (2019).
Novak et al., "Competitive adsorption and state of charge of halide ions in monolayer oxide film growth process at Pt anodes," J Chem Soc Faraday Trans, 77:2341-2359 (1981).
O'Reilly et al., "Catalytic methane monofunctionalization by an electrogenerated high-valent Pd intermediate," ACS Cent Sci, 3:2274-1179 (2017).
Olah, "Beyond oil and gas: The methanol economy**," Angew Chem Int Ed, 44:2636-2639 (2005).
Owen et al., "Kinetics and mechanism of methane, methanol, and dimethyl ether C—H activation with electrophilic platinum complexes," J Am Chem Soc, 128:2005-2016 (2006).
Promoppatum et al., "Identifying material and device targets for a flare gas recovery system utilizing electrochemical conversion of methane to methanol," ACS Sustainable Chem Eng, 4:1736-1745 (2016).
Ravi et al., "The direct catalytic oxidation of methane to methanol—a critical assessment," Angew Chem Int Ed, 56:16464-16483 (2017).

(56) References Cited

OTHER PUBLICATIONS

Scortichini et al., "Surface characterization of Pt electrodes using underpotential deposition of H and Cu," Journal of Catalysis, 79:138-146 (1983).

Sen et al., "Activation of methane and ethane and their selective oxidation to the alcohols in protic media," J Am Chem Soc, 116:998-1003 (1994).

Sen et al., "C—H activation in aqueous medium. The diverse roles of platinum (II) and metallic platinum in the catalytic and stoichiometric oxidative functionalization of organic substrates including alkanes," J Am Chem Soc, 114:6385-6392 (1992).

Shilov, A. E et al. "Activation and Catalytic Reactions of Saturated Hydrocarbons in the Presence of Metal Complexes; Catalysis by Metal Complexes," Kluwer Academic Publishers: Dordrecht, 2002; vol. 21.

Siegbahn et al., "Modeling the solvent sphere: Mechanism of the Shilov reaction," J Am Chem Soc, 118:4442-4450 (1996).

Snell et a., "Chloride inhibition of ethanol electrooxidation at a platinum electrode in aqueous acid solution [1]," Electrochimica Acta, 26(9):1339-1344 (1981).

Wang et al., "Advances in methane conversion processes," Catalysis Today, 285:147-158 (2017).

Weinberg et al., "Competitive oxidation and protonation of aqueous monomethylplatinum (II) complexes: a comparison of oxidants," Organometallics, 26:167-172 (2007).

Xu et al., "Electro-oxidation of a chloride complex of platinum (II) at a glassy carbon electrode," Journal of Electroanalytical Chemistry, 383:133-137 (1995).

Yadav et al., "Analysis of EIS technique and Nafion 117 conductivity as a function of temperature and relative humidity," Journal of Electrochemical Society, 159(3):B340-B346 (2012).

Young et al., "Complexes of ruthenium, rhodium, iridium, and platinum with tin(II) chloride," 5176-5189 (1964).

Zhao et al., "Recent advances in catalysts for direct methanol fuel cells," Energy Environ Sci, 4:2376-2753 (2011).

International Preliminary Report on Patentability for International Application No. PCT/US2020/022987 dated Sep. 16, 2021.

\* cited by examiner

CONTROLLED ELECTROCHEMICAL OXIDATION OF PT(II) IONS FOR CONTINUOUS METHANE-TO-METHANOL CONVERSION

RELATED APPLICATIONS

This application claims the benefit of priority to U.S. Provisional Patent Application No. 62/819,046, filed Mar. 15, 2019.

BACKGROUND

Methane is an abundant hydrocarbon resource that is often underutilized because of its low boiling point and chemical inertness. Thus, technologies for converting methane to liquid chemicals such as methanol would enable better utilization of this low-carbon resource.[1-3] Current methane valorization technologies rely on an indirect process involving initial steam reforming to $H_2$ and CO. The reforming step requires capital-intensive facilities that are not amenable to remote deployment.[4] Consequently, spontaneously released natural gas at oil wells is being flared at massive scales.[5,6] The development of mild, direct methane-to-methanol processes (Scheme 1) that can operate portably is expected to stem flaring as well as expand the versatility of natural gas.[7,8]

Scheme 1. Oxidation of methane to methanol.

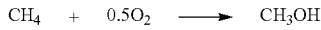

$$CH_4 + 0.5 O_2 \longrightarrow CH_3OH$$

While many homogeneous and heterogeneous systems have been investigated for methane-to-methanol conversion,[1,8,9] simple $Pt^{II}$ chloride salts in water, $Pt^{II}Cl_x(H_2O)_{(4-x)}^{(2-x)}$ (denoted collectively as $Pt^{II}$), offer unique advantages. The catalytic cycle (FIG. 1) is initiated by $Pt^{II}$ ions, which carry out reversible C—H activation of $CH_4$ to yield a $Pt^{II}$—$CH_3$ intermediate. This intermediate is then oxidized by $Pt^{IV}Cl_x(H_2O)_{(6-x)}^{(4-x)}$ (denoted collectively as $Pt^{IV}$) to generate a $Pt^{IV}$—$CH_3$ species that undergoes rapid reductive elimination to produce $CH_3OH$ or $CH_3Cl$, which is easily hydrolyzed to $CH_3OH$.

This system has the following advantages: first, the organometallic activation of methane offers superior selectivity for mono-oxidation compared to catalysts that operate via radical intermediates;[8,10-12] second, while most homogeneous catalysts that do organometallic activation require impractical[8] concentrated acid media for boosting the catalytic rate and selectivity,[13,14] $Pt^{II}$ operates in water. Along with the relatively low reaction temperature (>100° C.), these advantages position $Pt^{II}$ chloride salts, often referred to as "Shilov's catalyst," as privileged agents for methane-to-methanol conversion under mild conditions.

A critical drawback of Shilov's catalyst, as originally reported, is its requirement for a stoichiometric $Pt^{IV}$ oxidant, which is economically impracticable.[15] The key to developing an alternative oxidation strategy for this catalytic system is to achieve precise control over the driving force (thermodynamics) and/or rate (kinetics) of the oxidation reaction. In view of the catalytic cycle, there are two distinct approaches to the problem. First, $Pt^{IV}$ may be directly replaced by an alternative oxidant that can oxidize the $Pt^{II}$—$CH_3$ intermediate (FIG. 1, A). Success of this strategy requires an oxidant that (i) rapidly oxidizes the fleeting $Pt^{II}$—$CH_3$ intermediate before it can undergo protonation back to $Pt^{II}$+$CH_4$, and (ii) possesses a low enough redox potential to avoid oxidizing the $Pt^{II}$ catalyst to $Pt^{IV}$, which is inactive towards $CH_4$. The conflicting requirement for fast rates and low driving force places an inherent constraint on the oxidants that are viable. Second, one may employ $Pt^{IV}$ itself, which is an efficient oxidant for $Pt^{II}$—$CH_3$, as a redox mediator for the overall reaction (FIG. 1, B). Success of this strategy hinges on carefully matching the rate of $Pt^{IV}$ regeneration by $Pt^{II}$ oxidation to the rate of its consumption by methane functionalization. Rapid oxidation will progressively deplete the pool of $Pt^{II}$, retarding catalysis, whereas slow oxidation will induce irreversible decomposition of the $Pt^{II}$ to metallic $Pt^0$.[15,16] Thus, a viable alternate oxidant must achieve good control over the oxidation driving force and/or rate.

The inherent difficulty of fine-tuning oxidation using chemical reagents, has, presumably, contributed to the limited success in replacing stoichiometric $Pt^{IV}$. Notably, oxidants such as heteropoly acids, $CuCl_2$, $FeCl_3$, and $Br_2$ were identified as kinetically competent toward oxidation of $Pt^{II}$—$CH_3$ (FIG. 1, A).[17] These oxidants have achieved $Pt^{II}$-mediated oxidation of methane or a surrogate aliphatic substrate,[18-21] and some of them, being air-regenerable, have been employed in concert with $O_2$ to effect overall aerobic methane functionalization. However, none of these studies established long-term stability. For example, the combination of $CuCl_2$ and $O_2$ ultimately resulted in complete oxidation of $Pt^{II}$ to $Pt^{IV}$,[15] highlighting the difficulty of controlling the oxidation driving force. Studies aimed at mediating turnover via the $Pt^{II/IV}$ redox couple (FIG. 1, B) showed that $Cl_2$[22] and $H_2O_2$ are viable oxidants.[16] However, the $Pt^{II}$ oxidation rate was not actively modulated and, thus, continuous operation was not demonstrated. Furthermore, neither of these oxidants are air-regenerable or affordable for methanol production. In sum, a suitable alternative to stoichiometric $Pt^{IV}$ for sustained aqueous $Pt^{II}$-catalyzed methane-to-methanol conversion is needed.

SUMMARY

The present disclosure relates to a process for oxidizing a compound, comprising:
  (i) providing a reaction mixture, comprising water, a source of $Pt^{II}$ species at an initial concentration, a compound of formula $R^1$-$R^2$, an anion, and a Bronsted acid;
  (ii) applying electrical potential or electrical current to the reaction mixture at a temperature, thereby oxidizing the compound of formula $R^1$-$R^2$; and
  (iii) measuring the concentration of $Pt^{II}$ species in the reaction mixture;
  wherein the anion is chloride, fluoride, bromide, iodide, a carboxylate, nitrate, perchlorate, phosphate, or sulfate;
  the initial concentration of $Pt^{II}$ species is about 1 mM to about 10 M;
  $R^1$ is $C_1$-$C_{20}$ alkyl, $C_3$-$C_{12}$ cycloalkyl, $C_5$-$C_{10}$ heterocyclyl, $C_6$-$C_{12}$ aryl, or $C_5$-$C_{12}$ heteroaryl; and
  $R^2$ is H, —OH, —C(=O)H, or —C(=O)OH.

In some embodiments, the electrical potential is applied; and the electrical potential is adjusted to maintain the concentration of $Pt^{II}$ species at about 95% to about 105% of the initial concentration.

In certain embodiments, electrical current is applied; and the electrical current is adjusted to maintain the concentration of $Pt^{II}$ species at about 95% to about 105% of the initial concentration.

In some embodiments, the reaction mixture is contained within a reaction vessel comprising a working electrode, and a counter electrode, and, optionally, a reference electrode.

In certain embodiments, the reaction vessel further comprises a $Pt^{II}$ sensing electrode.

In some embodiments, the reaction vessel is a flow reaction vessel.

In certain embodiments, the concentration of $Pt^{II}$ species is measured potentiometrically.

In some embodiments, the concentration of $Pt^{II}$ species is measured with a $Pt^{II}$ sensing electrode. For example, the $Pt^{II}$ sensing electrode is selected from the group consisting of a Pt foil electrode, a Pt mesh electrode, a Pt wire electrode, and a platinized $Pt/H_2$ electrode.

In certain embodiments, the working electrode is selected from the group consisting of a Pt foil electrode, a Pt mesh electrode, an $Hg/HgSO_4$ electrode, an Ag/AgCl electrode, a Pt wire electrode, a platinized $Pt/H_2$ electrode, a calomel electrode, a fluorine-doped tin oxide electrode, an indium-doped tin oxide electrode, a glassy carbon electrode, a carbon black electrode, a pyrolytic graphite electrode, a graphite electrode, a carbon nanotube electrode, and a boron-doped diamond electrode. For example, the working electrode is a Pt foil electrode.

In some embodiments, the reference electrode is selected from the group consisting of a Pt foil electrode, a Pt mesh electrode, an $Hg/HgSO_4$ electrode, an Ag/AgCl electrode, a Pt wire electrode, a platinized $Pt/H_2$ electrode, a calomel electrode, a fluorine-doped tin oxide electrode, an indium-doped tin oxide electrode, a glassy carbon electrode, a carbon black electrode, a pyrolytic graphite electrode, a graphite electrode, a carbon nanotube electrode, and a boron-doped diamond electrode. For example, the reference electrode is an Ag/AgCl electrode.

In certain embodiments, the counter electrode is selected from the group consisting of a Pt foil electrode, a Pt mesh electrode, an $Hg/HgSO_4$ electrode, an Ag/AgCl electrode, a Pt wire electrode, a platinized $Pt/H_2$ electrode, a calomel electrode, a fluorine-doped tin oxide electrode, an indium-doped tin oxide electrode, a glassy carbon electrode, a carbon black electrode, a pyrolytic graphite electrode, a graphite electrode, a carbon nanotube electrode, and a boron-doped diamond electrode. For example, the counter electrode is a Pt mesh electrode.

In some embodiments, the counter electrode is immersed in a solution of an electron acceptor. For example, the electron acceptor is a proton or vanadyl sulfate. Alternatively, the counter electrode is an oxygen-consuming electrode.

In certain embodiments, the anion is chloride, fluoride, acetate, nitrate, perchlorate, phosphate, or sulfate. For example, the anion is chloride.

In some embodiments, the chloride is a constituent of a salt selected from the group consisting of NaCl, KCl, LiCl, CsCl, RbCl, $MgCl_2$, $CaCl_2$, $BaCl_2$, $NH_4Cl$, and HCl. For example, the salt is NaCl.

In certain embodiments, the source of $Pt^{II}$ species is selected from the group consisting of $K_2PtCl_4$, $Na_2PtCl_4$, $Li_2PtCl_4$, $H_2PtCl_4$, $(NH_4)_2PtCl_4$, $K_2PtBr_4$, $Na_2PtBr_4$, $Li_2PtBr_4$, $H_2PtBr_4$, $(NH_4)_2PtBr_4$, $K_2Pt(CN)_4$, $Na_2Pt(CN)_4$, $Li_2Pt(CN)_4$, $H_2Pt(CN)_4$, $(NH_4)_2Pt(CN)_4$, $K_2PtCl_6$, $Na_2PtCl_6$, $Li_2PtCl_6$, $H_2PtCl_6$, $(NH_4)_2PtCl_6$, $Pt(NH_3)_4Cl_2$, $Pt(NH_3)_4(NO_3)_2$, $Pt(NH_3)_4(OH)_2$, $Pt(NH_3)_4Cl_4$, and $PtO_2$. For example, the source of $Pt^{II}$ species is $K_2PtCl_4$.

In some embodiments, the Bronsted acid is selected from the group consisting of $H_2SO_4$, HCl, $HNO_3$, $H_3PO_4$, $HClO_4$, and a carboxylic acid. For example, the Bronsted acid is HCl.

In certain embodiments, the temperature is about 20° C. to about 500° C. For example, the temperature is about 150° C. to about 300° C.

In some embodiments, electrical current is applied at a constant current.

In certain embodiments electrical potential is applied under constant potential conditions.

In some embodiments, the compound of formula $R^1$-$R^2$ is an alkane or a cycloalkane.

In certain embodiments, the compound of formula $R^1$-$R^2$ is methane.

In certain embodiments the compound of formula $R^1$-$R^2$ is oxidized to an alcohol. For example, the alcohol is a diol or a polyol.

DETAILED DESCRIPTION

Overview

Figure 1:
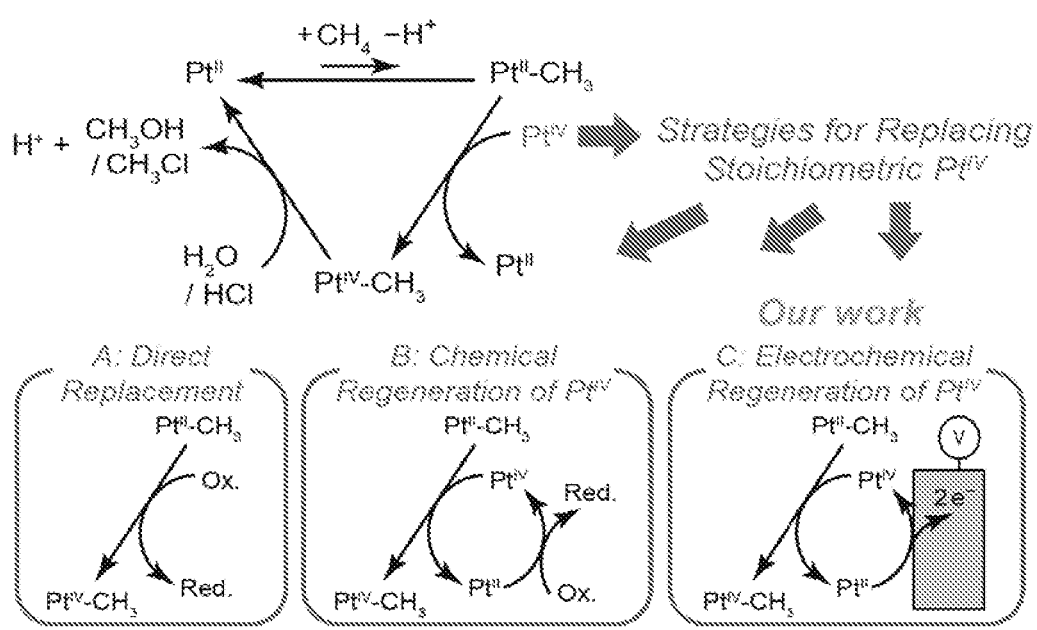
FIG. 1 depicts catalytic cycle for the functionalization of methane by aqueous Pt salts (Shilov's catalyst) and different strategies to overcome the stoichiometric use of $Pt^{IV}$

The present disclosure relates to an electrochemical solution to the problem of sustained aqueous $Pt^{II}$-catalyzed methane-to-methanol conversion, exploiting the unparalleled control over oxidation rate and driving force that electrochemistry affords. While direct electrooxidation of the fleeting $Pt^{II}$—$CH_3$ intermediate is unfeasible due to the small fraction of reaction solution volume in contact with the electrode surface, the electrochemical oxidation of $Pt^{II}$ could be carried out at precisely controlled rates to enable stable and continuous $Pt^{II}$-catalyzed methane oxidation (FIG. 1, C). In addition, coupling this half-reaction with an oxygen reducing cathode would render the process aerobic in net. Despite its attractiveness, there exist a paucity of examples of this approach. One report applied electrochemical oxidation in the presence of $Pt^{II}$, heteropoly acids, and $O_2$ to achieve 1.4 turnovers for methanol production, but no information about the mechanism or stability of the system was provided.[23] Earlier, a similar scheme was employed to oxidize a test substrate, p-toluenesulfonic acid; while 11 turnovers of the $Pt^{II}$ catalyst was attained, deposition of $Pt^0$ was observed with increasing reaction times.[24] A particular impediment to electrochemical turnover of the aqueous $Pt^{II}$ catalyst is the general sluggishness of two-electron $Pt^{II/IV}$ oxidation at an electrode.[25,26] Previously, electrochemical oxidation of $Pd^{II}$ salts to generate a highly electrophilic $Pd_2^{III,III}$ species was reported, resulting in the conversion of methane to methanol precursors.[27] While this system showed exceptional rates and high selectivity, it required concentrated acid media that restrict practical utility. In the present disclosure, Pt electrodes that catalyze facile oxidation of $Pt^{II}$ to $Pt^{IV}$ [28] are combined with in situ modulation of electric current to achieve continuous, steady-state methane oxidation over the course of 30 hours. Methanol and methyl chloride as the principal products with >80% combined selectivity, demonstrating continuous $Pt^{II}$-catalyzed electrochemical methane oxidation reaction (EMOR).

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 1 to 20. Alkyl groups may be optionally substituted with one or more substituents, for example, halogen, alkyl, cycloalkyl, hydroxyl, amino, heterocyclyl, alkoxy, and the like.

"Alkane" refers to a fully saturated cyclic or acyclic, branched or unbranched carbon chain molecule having the number of carbon atoms specified, or up to 30 carbon atoms if no specification is made. For example, alkane of 1 to 8 carbon atoms refers to moieties such as methane, ethane, propane, butane, pentane, hexane, heptane, and octane, and those molecules which are positional isomers of these molecules. Alkane of 10 to 30 carbon atoms includes decane, undecane, dodecane, tridecane, tetradecane, pentadecane, hexadecane, heptadecane, octadecane, nonadecane, eicosane, heneicosane, docosane, tricosane and tetracosane. In certain embodiments, a straight chain or branched alkane has 30 or fewer carbon atoms in its backbone (e.g., $C_1$-$C_{30}$ for straight chains, $C_3$-$C_{30}$ for branched chains), and more preferably 20 or fewer. Alkanes may be optionally substituted with one or more substituents, for example, halogen, alkyl, cycloalkyl, hydroxyl, amino, heterocyclyl, alkoxy, and the like.

"Cycloalkane" means mono- or bicyclic or bridged or spirocyclic, or polycyclic saturated carbocyclic rings, each having from 3 to 20 carbon atoms. Preferred cycloalkanes have from 3-12 carbon atoms in their ring structure. Cycloalkanes may be optionally substituted with one or more substituents, for example, halogen, alkyl, hydroxyl, amino, heterocyclyl, alkoxy, and the like.

The terms "alkoxyl" or "alkoxy" as used herein refers to an alkyl group, as defined above, having an oxygen moiety attached thereto. Representative alkoxyl groups include methoxy, ethoxy, propoxy, tert-butoxy, and the like.

The terms "amine" and "amino" are art-recognized and refer moieties that can be represented by the formulae:

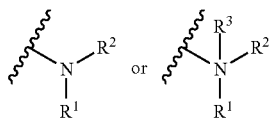

wherein $R^1$, $R^2$ and $R^3$ each independently represent an alkyl, an aryl, a cycloalkyl, or a heterocyclyl.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 6- to 12-membered rings The term "aryl" also includes polycyclic ring systems having two or more cyclic rings in which two or more carbons are common to two adjoining rings wherein at least one of the rings is aromatic. Heteroaryl groups include substituted or unsubstituted aromatic 3- to 12-membered ring structures, more preferably 5- to 12-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic.

The term "halo", "halide", or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The terms "heterocyclyl" or "heterocyclic group" refer to 3- to 12-membered ring structures, more preferably 5- to 12-membered rings, whose ring structures include one to four heteroatoms. Heterocycles can be monocyclic, bicyclic, spirocyclic, or polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted or unsubstituted.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

Structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention.

For purposes of this invention, the chemical elements are identified in accordance with the Periodic Table of the Elements, CAS version, Handbook of Chemistry and Physics, 67th Ed., 1986-87, inside cover.

Identification of a Suitable Electrode for $Pt^{II}$-Catalyzed Electrochemical Methane Oxidation Reaction (EMOR).

The electrochemical mediation scheme put forward above (FIG. 1, C) requires an electrode capable of oxidizing $Pt^{II}$ to $Pt^{IV}$. In view of the high $Pt^{II/IV}$ oxidation potential ($E^0$=0.68 V vs SHE for $Pt^{II}Cl_4^{2-}/Pt^{IV}Cl_6^{2-}$)[29] and the acidic environment required for stability of the Pt ions,[30] the initial investigation was focused on carbon, fluorine-doped tin oxide (FTO), and Pt electrodes as possible candidates. Whereas carbon and FTO electrodes displayed progressive deactivation and/or sluggish $Pt^{II}$ oxidation kinetics (see Example 1), Pt electrodes showed facile oxidation of $Pt^{II}$ at modest potentials. In 0.5 M $H_2SO_4$, the Pt electrode displays the typical voltammetric features associated with hydrogen underpotential deposition (H UPD) and oxide formation at low and high potentials, respectively (FIG. 2, (a), black).[31,32] Upon addition of 1 mM $Pt^{II}$, a reversible wave appears at $E_{p,a}$=1.1 V and $E_{p,c}$=0.8 V (FIG. 2, (b), blue). The appearance of this wave is also accompanied by a suppression in the background Pt oxide wave. Pt oxide formation is known to be inhibited by $Cl^-$ adsorption to the surface[33] and, thus, it is proposed that this suppression results from adsorption of $Cl^-$ dissociated from the $Pt^{II}Cl_4^{2-}$ ions (see Example 2). As sustained methanol production requires $Cl^-$ ions (see below), the voltammetric response of $Pt^{II}$ was also examined in the presence of 10 mM $Cl^-$. Whereas the $Pt^{II}$ oxidation wave is largely unaffected by the additional $Cl^-$, the cathodic wave associated with $Pt^{IV}$ back-reduction is significantly suppressed. These observations are in line with previous literature on $Pt^{II/IV}$ oxidation at Pt electrodes that invokes an inner-sphere electron transfer (ISET) mechanism involving transfer of a surface-adsorbed $Cl^-$ to $Pt^{II}$ during the oxidation reaction.[28] Thus, higher surface coverage of $Cl^-$ induced by higher [$Cl^-$] will have a negligible impact on $Pt^{II}$ oxidation, but the back-reduction of $Pt^{IV}$, which requires $Cl^-$ transfer back to the electrode surface, will be inhibited. This inner-sphere mechanism explains why Pt electrodes display superior $Pt^{II}$ electro-oxidation kinetics compared to carbon or FTO.

Electro-Oxidation of $Pt^{II/IV}$ at the Elevated Temperatures Required for Methane Activation by $Pt^{II}$.

Figure 2:
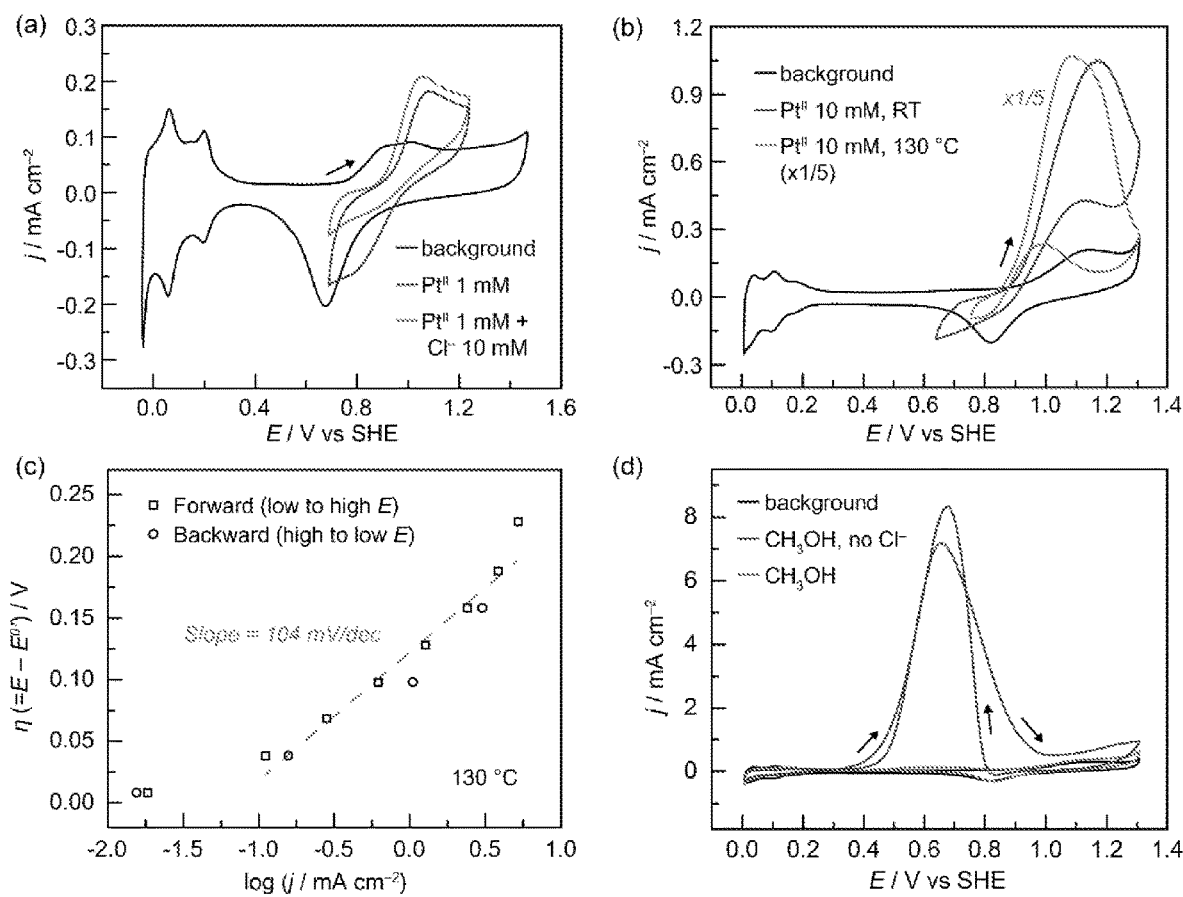
FIG. 2 depicts cyclic voltammograms obtained on a Pt disk electrode at room temperature in 0.5 M $H_2SO_4$; (black) background, (blue) 1 mM $K_2Pt^{II}Cl_4$, and (red) 1 mM $K_2Pt^{II}Cl_4$+ 10 mM NaCl (a); cyclic voltammograms obtained on a Pt wire electrode in 0.5 M $H_2SO_4$+10 mM NaCl; (black) background and (blue) 10 mM of $K_2Pt^{II}Cl_4$ at room temperature, and (red) 10 mM of $K_2Pt^{II}Cl_4$ at 130° C. (b); and Tafel plot at 130° C. for $Pt^{II}$ electro-oxidation (c). The solution contained 5 mM each of $K_2Pt^{II}Cl_4$ and $Na_2Pt^{IV}Cl_6$ in 0.5 M $H_2SO_4$+10 mM NaCl. $E_{eq}$ (=0.829 V vs SHE) was obtained from the open-circuit potential (see SI for raw data); and cyclic voltammograms obtained on a Pt wire electrode in 0.5 M $H_2SO_4$+10 mM NaCl at 130° C.; (black) background, (blue) 30 mM $CH_3OH$ without the 10 mM NaCl, and (red) 30 mM $CH_3OH$ (d). All scan rates=100 mV $s^{-1}$.
Figure 3:
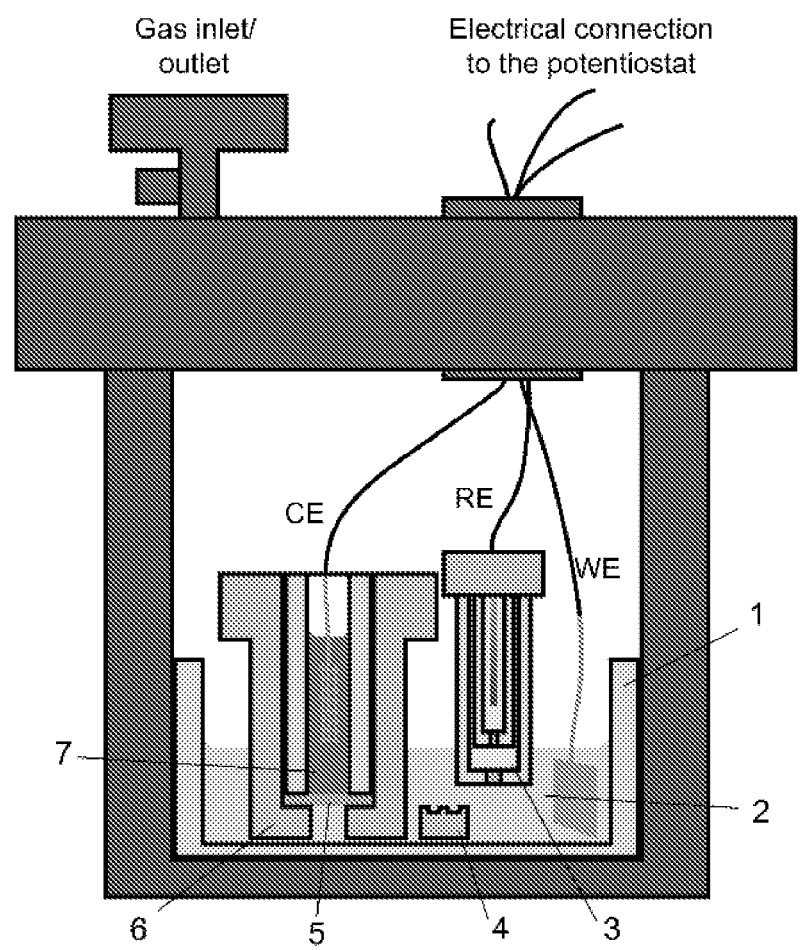
FIG. 3 depicts a schematic diagram for a high-pressure, three-electrode, two-compartment electrochemical cell for EMOR. WE: Pt foil working electrode, RE: Ag/AgCl reference electrode, CE: Pt mesh counter electrode. 1: Glass cell, 2: working solution containing the Pt ions, 3: fritted tubes for housing the RE, 4: PTFE stir bar, 5: $H^+$-conducting membrane separating the counter compartment, 6: PTFE body holding the membrane stack, and 7: counter compartment solution containing $(V^{IV}O)(SO_4)$ as the sacrificial electron acceptor.

These experiments were conducted above the boiling point of water and were, therefore, carried out in a high-pressure electrochemical cell (FIG. 3). As shown in FIG. 2, (b), red, high $Pt^{II}$ oxidation current flowed at 130° C.; the 5-fold enhancement in current and approximately 100 mV negative shift in $E_{p,a}$ reflect faster mass transport and electrode kinetics compared to room temperature. The decrease in current at E>1.1 V (FIG. 4(b)) is attributed to the formation of surface oxides that inhibit the inner-sphere $Pt^{II}$ oxidation. This inhibition is particularly pronounced at high [$Pt^{II}$] and high temperatures. The dependence of $Pt^{II}$ oxidation current on electrochemical driving force was also examined (FIG. 2, (c)). Keeping the potential below Pt oxide formation, <1.1 V, the steady-state current increased 10-fold per 104 mV of additional overpotential ($\eta$=E–$E_{eq}$). This Tafel slope corresponds to a rate-limiting one-electron transfer with a transfer coefficient of 0.42, in agreement with the aforementioned mechanism.[34] These results show that the Pt electrodes are capable of facile oxidation of $Pt^{II}$ at elevated temperatures.

Pt electrodes were also capable of sustained and efficient $Pt^{II/IV}$ oxidation. Bulk electrolysis of a stirred solution was conducted at 130° C. by applying a constant potential below 1.1 V. After chronoamperometry at 0.874, 0.924 and 0.974 V for 77, 40 and 17 min, respectively, half of the $Pt^{II}$ ions in the initial solution were converted to $Pt^{IV}$ ions as determined by UV-Vis analysis. At all three potentials examined, $Pt^{IV}$ was generated with 100% Faradaic efficiency (Table 1).

TABLE 1

Results of bulk electrolysis of $Pt^{II}$ to $Pt^{IV}$ at 130° C. with stirring at 200 rpm. The solution initially contained 5 mM of $K_2Pt^{II}Cl_4$, 5 mM $Na_2Pt^{IV}Cl_6$ and 10 mM NaCl in 0.5M $H_2SO_4$ (initial amount of $Pt^{II}$ = 110-115 μmol).

| E (V vs. SHE) | Duration (min) | $e^-$ passed (μmol) | $\Delta Pt^{IV}$ (μmol) | FE (%) |
| --- | --- | --- | --- | --- |
| 0.874 | 78 | 111.4 | 55.7 | 103% |
| 0.924 | 40 | 109 | 54.5 | 106% |
| 0.974 | 17 | 115 | 57.5 | 103% |

Sustained methane oxidation catalysis will lead to a progressive rise in methanol concentration in the reactor over time. Thus, in addition to supporting facile $Pt^{II/IV}$ oxidation, the electrode must be inert towards further oxidation of the $CH_3OH$ product. This is a particular concern for Pt, which is the standard electrocatalyst for oxidation of $CH_3OH$ to $CO_2$.[35] Indeed, in 0.5 M $H_2SO_4$ at 130° C., addition of 30 mM $CH_3OH$ gives rise to the well-known anodic features associated with $CH_3OH$ electro-oxidation (FIG. 2, (d), blue).[36] Remarkably, upon addition of 10 mM of $Cl^-$, this $CH_3OH$ oxidation feature is almost completely suppressed (FIG. 2, (d), red) over the entire potential range examined. This suppression is ascribed to surface adsorption of $Cl^-$ ions.[37] Additional control experiment confirmed that the non-electrochemical oxidation of $CH_3OH$ catalyzed on metallic $Pt^{38}$ is also negligible under the disclosed conditions. These data indicate that, fortuitously, the presence of $Cl^-$ serves to simultaneously promote $Pt^{II/IV}$ oxidation and suppress surface-catalyzed oxidation of the methanol product. Together, these studies establish that Pt electrodes are suitable for EMOR.

Sustained Methane Oxidation Catalysis Via Dynamic Electrochemical Control of the $Pt^{II}$:$Pt^{IV}$ Ratio.

The above studies provide the basis for carrying out continuous methane-to-methanol oxidation catalysis via electrochemical regeneration of $Pt^{IV}$ (FIG. 1, C). The EMOR was carried out in a high-pressure cell which consisted of a modified Parr reactor with electrical feedthroughs (FIG. 3; Example 3). The working compartment was charged with 3 mM $Pt^{II}$ and 7 mM $Pt^{IV}$ in 0.5 M $H_2SO_4$+10 mM NaCl (see Example 3). The counter compartment, separated by a $H^+$-conducting membrane stack, contained 3 M vanadyl sulfate (($V^{IV}O$)($SO_4$)) as a sacrificial oxidant to be reduced at the cathode. In a practical device, oxygen could be supplied to the cathode, but given the low solubility of $O_2$ and complications of co-pressurizing the cell with $O_2$, the vanadyl ion can be used as a surrogate. The highly soluble and fairly inert vanadyl ions enabled examination of long-term electrolysis. This counter reaction prevented $H_2$ evolution, which must be avoided in this configuration due to the irreversible reduction of $Pt^{II}$ to $Pt^0$ by $H_2$; however, in a well-engineered system with good gas stream separation, $H_2$ may be deliberately generated as a useful byproduct. The solutions and the cell were purged to remove $O_2$ prior to pressurization with 500 psi of methane. Following heating and temperature stabilization at 130° C., electrolysis was initiated to continuously re-oxidize $Pt^{II}$ during methane functionalization catalysis. Constant current (galvanostatic)

electrolysis was chosen over constant potential (potentiostatic) electrolysis to better match the conditions of practical industrial electrolysis.

Careful choice of the applied current is critical for sustained catalysis. In order to maintain a constant $Pt^{II}:Pt^{IV}$ ratio over the course of the reaction, the rate of $Pt^{II}$ oxidation at the electrode must match the rate of methane oxidation catalysis in the solution. At a fixed rate of $Pt^{II/IV}$ oxidation, a simple mathematical derivation shows that any small difference between the two rates will increase exponentially over time (see Example 4). Thus, the applied current must constantly match the rate of catalysis to maintain a steady ratio of $Pt^{II}:Pt^{IV}$. To achieve this matching, it is necessary to monitor $[Pt^{II}]$ and adjust the current (i) accordingly. In order to achieve this, the open-circuit potential (OCP) of the working compartment was employed as an in situ probe of the instantaneous $Pt^{II}:Pt^{IV}$ ratio in solution. In the reactor, the $Pt^{II}$ and $Pt^{IV}$ ions exist in various ligated states ($Pt^{II}Cl_x(H_2O)_{(4-x)}^{(2-x)}$, $Pt^{IV}Cl_x(H_2O)_{(6-x)}^{(4-x)}$), each pair of which has different redox potentials. Assuming that [Cl⁻] is constant, the following modified form of the Nernst equation may be derived as shown in Scheme 2:

$$E = E^C + \frac{RT}{2F}\ln\frac{[Pt^{IV}]}{[Pt^{II}]}; E^C = E^{0\prime\prime} + \frac{RT}{2F}\ln\frac{1}{[Cl^-]^n}.$$ Scheme 2

Modified Nernst equation used for determining
$Pt^{II}:Pt^{IV}$ ratios potentiometrically.

where $E^{0\prime\prime}$ and n represents the weighted average of the redox potentials and chloride stoichiometries, respectively. Thus, using the equation in Scheme 2, the instantaneous $Pt^{II}:Pt^{IV}$ ratios can be estimated potentiometrically. $E^C$ can be determined from the initial OCP reading and the known initial $Pt^{II}:Pt^{IV}$ ratio.

Figure 4:
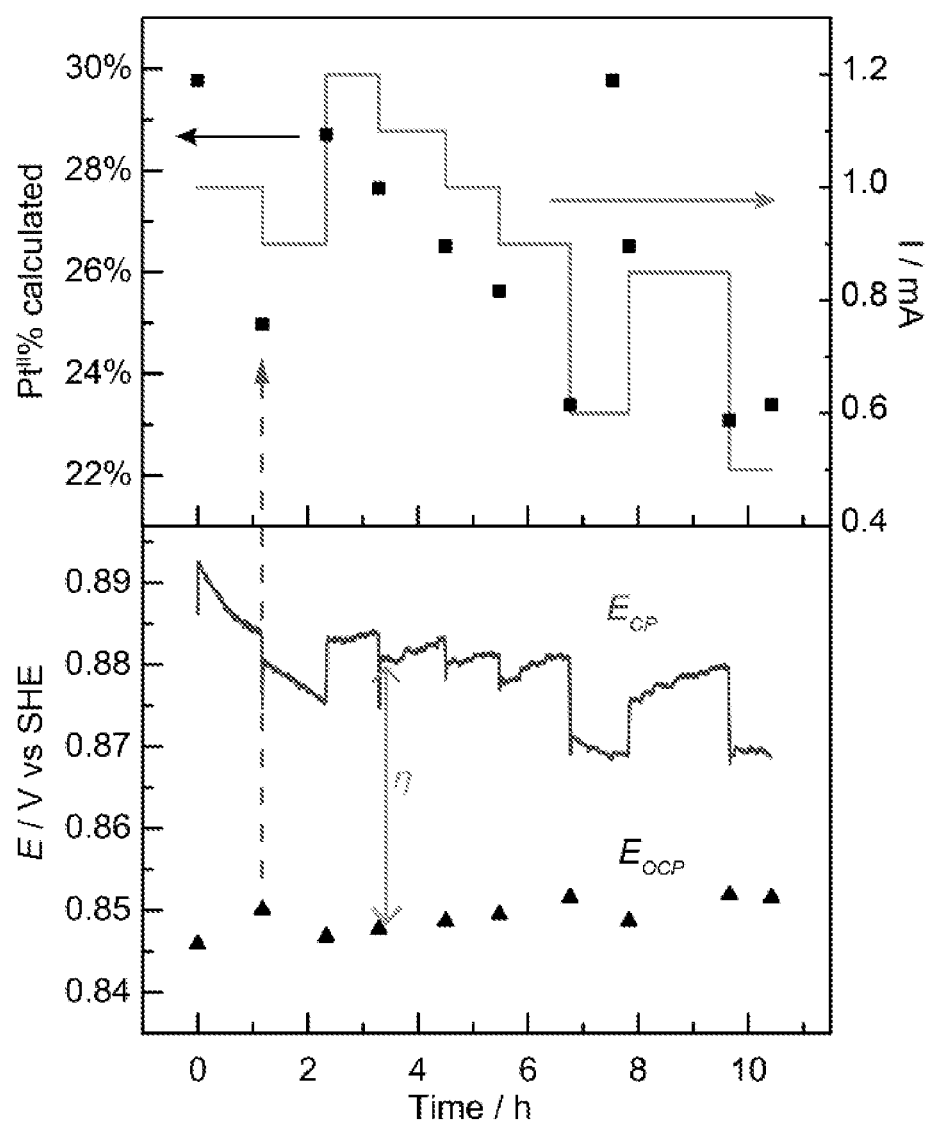
FIG. 4 depicts representative electrochemical data plots recorded during an EMOR trial (the 10.5 h-long trial in Table 1). The open-circuit potential ($E_{OCP}$) reading at approx. 1 h time intervals (bottom, black triangles) were used to calculate the $Pt^{II}$% in the solution (top, black squares). This was in turn used to determine how much current to pass (top, red line). The electrode potential during the constant current polarization ($E_{CP}$) was also recorded (bottom, blue line).

FIG. 4 shows the electrochemical data recorded during a typical EMOR trial with periodic OCP monitoring and adjustment of the current. To aid interpretation, the $Pt^{II}:Pt^{IV}$ ratio was converted to the percentage of $Pt^{II}$ ions ($Pt^{II}\%$), defined as $[Pt^{II}]/([Pt^{II}]+[Pt^{IV}])$. In a representative reaction, after passing 1.0 mA of current for 1 h, the $Pt^{II}\%$ decreased from 30% to 25%. This led to adjustment of the current to 0.9 mA, and after another 1 h, the $Pt^{II}\%$ rose to 29%. This process of quantifying the $Pt^{II}\%$ in the solution and adjusting the current to maintain a roughly constant $Pt^{II}\%$ was repeated periodically until the reaction was terminated. Incidentally, while the present reactor was too congested to conveniently add a fourth electrode, incorporation of a separate $Pt^{II}$-sensing electrode could allow, in principle, for real-time feedback modulation of i. Any one of a variety of electrodes may be used to determine on a continuous basis the real-time concentration of the $Pt^{II}$ ions; for example, suitable electrodes include an $Hg/HgSO_4$ electrode, an Ag/AgCl electrode, a Pt wire electrode, a platinized $Pt/H_2$ electrode, and a calomel electrode.

The potential required for electrolysis ($E_{CP}$, CP=chronopotentiometry) equals the equilibrium electrode potential (OCP) plus the magnitude of overpotential (η) applied. By definition, η is the difference between the applied potential ($E_{CP}$) and $E_{OCP}$, as marked with green arrows in FIG. 4. Over multiple trials, a steady decrease in η was consistently observed during the initial 2-3 hours of each electrolysis, which was attributed to a slow initial electrode activation process. After stabilization of the electrode activity, η was ca. 20-40 mV, at an average current of around 0.9 mA. Normalizing by the electrode surface area, an average current density was estimated to be 0.09 mA/cm². This is in line with the previously obtained Tafel plot (FIG. 2, (c)) after considering the difference in $[Pt^{II}]$ (5 mM in the Tafel plot, approx. 3 mM in the EMOR trials). For a different reactor configuration, the magnitude of r will be different because the current density required for steady-state catalysis is an extrinsic parameter that depends on various parameters such as the electrode area and solution volume (see Example 5). Importantly, because the rate of $Pt^{II}$ electro-oxidation at any i is proportional to $[Pt^{II}]$, the $[Pt^{II}]$ can be increased to increase the overall rate of catalysis without requiring additional overpotential.

Independent quantification of the $Pt^{II}:Pt^{IV}$ ratio at the end of the EMOR confirmed the power of in situ current modulation. At the end of each reaction, $[Pt^{II}]$ and $[Pt^{IV}]$ in the working compartment was measured by UV-Vis spectroscopy. Despite a wide variation in reaction time (5-29 h) and consequently turnover number (see below), UV-Vis analysis confirmed that the final $Pt^{II}\%$ (19-23%) values were all similar (Table 1). These values are somewhat lower than the initial $Pt^{II}\%$ (30%), reflecting the preference to err on the side of lower $Pt^{II}\%$ to prevent irreversible $Pt^0$ deposition (see below). Interestingly, despite the agreement in final $Pt^{II}\%$ values, $\Delta OCP$ (=$OCP_{last}-OCP_{first}$), which should reflect the final $Pt^{II}\%$ according to the equation in Scheme 2, was more negative for longer reactions by up to 14 mV. This may be due to decreasing [Cl⁻] in the reaction solution as a result of $CH_3Cl$ formation. Despite this additional long-term effect, changes in the OCP between constant-current intervals provided a faithful indication of whether the $Pt^{II}\%$ was increasing or decreasing, allowing for appropriate adjustment of i. Together, these results demonstrate that the $Pt^{II}\%$ can indeed be maintained over long time durations of catalysis through dynamically-controlled electrochemical oxidation.

Careful control of the $Pt^{II}:Pt^{IV}$ ratio during the reaction is essential for another reason: $Pt^{IV}$ ions suppress the irreversible decomposition of $Pt^{II}$ to $Pt^0$.[15,39] Indeed, at the end of all of the EMOR trials, the bulk reaction solutions contained no visible $Pt^0$ precipitates. Only a few adventitious $Pt^0$ deposits were observed on the reactor surfaces and crevices where mass transport was restricted and replenishment of $Pt^{IV}$ was impeded (see Example 6). Although an extensive discussion of $Pt^0$ deposition mechanisms is beyond the scope of the current work, the present results are consistent with the proposal that maintenance of a sufficient concentration of $Pt^{IV}$ prevents $Pt^0$ formation.

Analysis of methane oxidation products from the EMOR reactor. Operation of the EMOR reactor using the feedback modulation procedure described above allowed for continuous functionalization of methane (Table 2 and FIG. 5).

TABLE 2

Results of EMOR trials at T = 130° C. and $P_{CH4}$ = 675 psi. Initial [$Pt^{II}$] and [$Pt^{IV}$] in the working solution were 3 mM and 7 mM, respectively, and the solution volume was 23 mL. The electrochemically active surface area of the Pt working electrode was 10.3 cm$^2$.

| Time$^a$ | $i_{ave}^b$ | $\Delta OCP^c$ | Final | Product (µmol (rel. fraction)) | | | | | approx. TON$^e$ | | approx. TOF$^e$ (h$^{-1}$) | |
|---|---|---|---|---|---|---|---|---|---|---|---|---|
| (h) | (mA) | (mV) | [$Pt^{II}$] % | $CH_3OH$ | $CH_3Cl$ | $CH_2(OH)_2^d$ | HCOOH | $CO_2$ | $CH_3X$ | Total | $CH_3X$ | Total |
| 4.9 | 1.19 | 7.9 | 22% | 60.5 (72%) | 20.1 (24%) | 2.2 (3%) | 0.1 (0%) | 1.1 (1%) | 1.4 | 1.6 | 0.29 | 0.32 |
| 10.5 | 0.88 | 5.7 | 19% | 93.7 (71%) | 27.9 (21%) | 5.1 (4%) | 1.2 (1%) | 4.4 (3%) | 2.3 | 2.9 | 0.21 | 0.27 |
| 18.4 | 1.00 | −2.8 | 22% | 205.4 (72%) | 44.8 (16%) | 21.9 (8%) | 2.9 (1%) | 12.2 (4%) | 4.5 | 6.3 | 0.24 | 0.34 |
| 29.3 | 0.91 | −6.0 | 23% | 268.0 (69%) | 52.0 (13%) | 36.4 (9%) | 7.2 (2%) | 24.1 (6%) | 5.8 | 9.3 | 0.20 | 0.32 |

$^a$The length of time the reactor was at the designated temperature, which spanned from ~80 minutes after the start of heating to the time at which the reactor was removed from the oil bath.
$^b i_{ave}$ was calculated by dividing the total charge passed by the reaction time.
$^c \Delta OCP$ is the difference between the first and last OCP readings (=$OCP_{last} - OCP_{first}$).
$^d$The hydrated form of formaldehyde, which is the predominant form of formaldehyde in the acidic pH employed.
$^e$The TONs were determined from dividing the µmol of product by the average of the initial and final µmol of $Pt^{II}$ for each reaction. The TOFs were obtained by dividing the TON by the time duration of each reaction. The total number of turnovers were calculated by assuming that all oxidation reactions were catalyzed by $Pt^{II}$: the total number of oxidizing equivalent were calculated as (µmol$_{CH3OH}$ + µmol$_{CH3Cl}$ + 2 * µmol$_{CH2(OH)2}$ + 3 * µmol$_{HCOOH}$ + 4 * µmol$_{CO2}$) and this sum was divided by the average µvmol$_{PtII}$ to determine total TON. For $CH_3X$-specific turnovers, only (µmol$_{CH3OH}$ + µmol$_{CH3Cl}$) was divided by µmol$_{PtII}$.

In all cases, $CH_3OH$ is observed as the majority product in 69-72% yield (Table 2). Appreciable quantities of $CH_3Cl$ are also observed with a yield that decreases from 24 to 13% as the reaction time increases (Table 2). Small amounts of overoxidized products ($CH_2(OH)_2$, HCOOH and $CO_2$) were observed in less than 20% combined yield. Taking these overoxidized products to represent $Pt^{II}$-catalyzed oxidation of $CH_3OH$ by 1, 2 and 3-equivalents of $Pt^{IV}$, respectively, the overall Faradaic efficiencies were in excess of 90% in all cases (Table 3).

TABLE 3

Estimated Faradaic efficiencies of different reactor trials.

| Time (hr) | Faradaic Efficiency |
|---|---|
| 4.9 | 90.6% |
| 10.5 | 96.4% |
| 18.4 | 97.8% |
| 29.3 | 94.0% |
| 10.5 (5x concentrations) | 101.4% |

The per-$Pt^{II}$ turnover numbers could not be rigorously determined due to minor fluctuations in [$Pt^{II}$] over the course of the reaction (see above), but approximate values were calculated from the known initial and final $Pt^{II}$ amounts. For the longest trial, TON values of 6 and 9 for monofunctionalized products ($CH_3X = CH_3OH$ and $CH_3Cl$) and total oxidation events were obtained, respectively (Table 2). The TOF for $CH_3X$, estimated to be 0.2-0.3 h$^{-1}$, showed a decreasing trend with increasing reaction time due to the overoxidation of $CH_3OH$. In contrast, the TOF for total oxidation events was relatively constant at ca. 0.3 h$^{-1}$ for different reaction times. Together, these observations demonstrate that electrochemical re-oxidation effectively sustains $Pt^{II}$-based methane functionalization catalysis.

Figure 5:
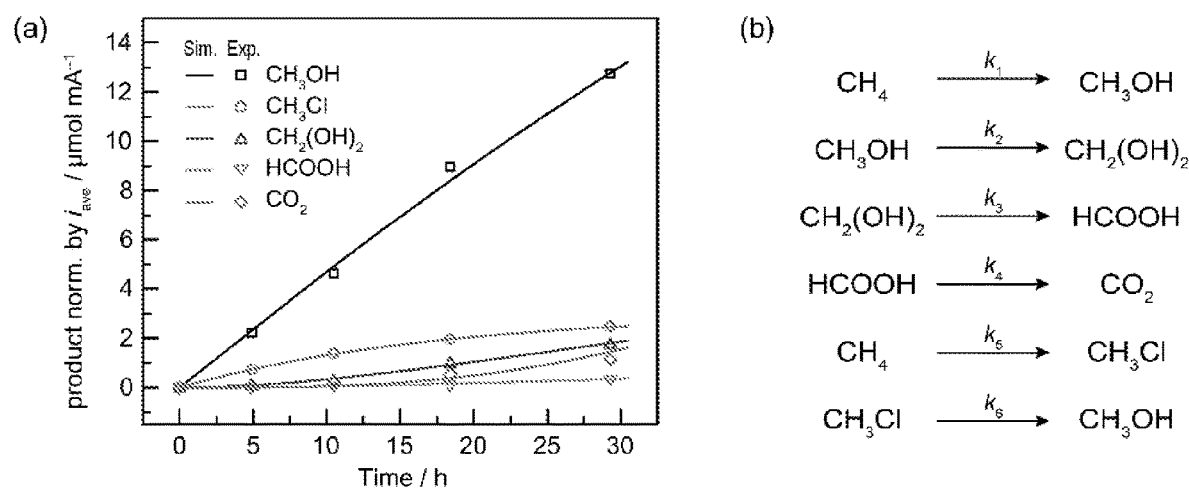
FIG. 5 depicts a plot demonstrating mounts of methane oxidation products from EMOR versus reaction time (a). Each point represents a different trial in Table 1, and the product concentrations were normalized by $i_{ave}$ of each trial. The lines represent fitting with the set of suggested reactions (b).

Combining the four trials in Table 2, FIG. 5, (a) visualizes the temporal progression of EMOR. These data were fit to the set of reactions suggested earlier: oxidation of $CH_4$ to $CH_3OH$ and $CH_3Cl$, hydrolysis of $CH_3Cl$ to $CH_3OH$, and subsequent oxidation of $CH_3OH$ to $CH_2(OH)_2$, HCOOH, and $CO_2$ (FIG. 5, (b)). While the fitted apparent rate constants (Table 4) for $CH_2(OH)_2$ and HCOOH oxidation show deviation from values separately determined outside the reactor, the fitted values for $CH_4$ and $CH_3OH$ oxidation are in good agreement with those independent measurements. Thus, this simple model provides a reasonable description of the methane oxidation processes taking place during EMOR.

TABLE 4

Rate constants from fitting experimental data with the mechanism in FIG. 5, (b).

| | $k_1$ | $k_2$ | $k_3$ | $k_4$ | $k_5$ | $k_6$ |
|---|---|---|---|---|---|---|
| Value (mM$^{-1}$ hr$^{-1}$) | $1.1 \times 10^{-2}$ | $1.9 \times 10^{-2}$ | $8.5 \times 10^{-2}$ | $4.0 \times 10^{-1}$ | $3.9 \times 10^{-3}$ | $5.7 \times 10^{-2}$ |

An electrochemical approach for continuous methane-to-methanol conversion using aqueous $Pt^{II}$ catalysts has been establishes. Cl-adsorbed Pt surfaces were shown to be competent for the inner-sphere two-electron oxidation of $Pt^{II}$ to $Pt^{IV}$ while inert toward parasitic oxidation of the methanol product. In situ potential measurements and current modulation allowed us to carry out continuous steady-state catalysis by maintaining the $Pt^{II}$:$Pt^{IV}$ ratio. While the test reactors were run up to 30 h, further reactor engineering to incorporate automatic real-time current modulation, enhance solution mixing, and rigorously separate the anode and cathode compartments should allow for extended operation. Moreover, integration of an oxygen-consuming counter electrode will enable net aerobic methane-to-methanol conversion. Examples of oxygen-consuming electrodes are disclosed in the following U.S. patents: U.S. Pat. Nos. 10,202,700; 9,163,318; 9,118,082; and 4,603,118; which are each incorporated herein by reference in their entirety.

While additional challenges must be overcome in order to realize practical $Pt^{II}$-catalyzed methane conversion,[15] it is believed that the electrochemical approach developed here will enable continued progress toward practical technologies for aerobic methane valorization.

The present disclosure relates to a process for oxidizing a compound, comprising:
(i) providing a reaction mixture, comprising water, a source of $Pt^{II}$ species at an initial concentration, a compound of formula $R^1$-$R^2$, an anion, and a Bronsted acid;
(ii) applying electrical potential or electrical current to the reaction mixture at a temperature, thereby oxidizing the compound of formula $R^1$-$R^2$; and
(iii) measuring the concentration of $Pt^{II}$ species in the reaction mixture;

wherein the anion is chloride, fluoride, bromide, iodide, a carboxylate, nitrate, perchlorate, phosphate, or sulfate;

the initial concentration of $Pt^{II}$ species is about 1 mM to about 10 M;

$R^1$ is $C_1$-$C_{20}$ alkyl, $C_3$-$C_{12}$ cycloalkyl, $C_5$-$C_{10}$ heterocyclyl, $C_6$-$C_{12}$ aryl, or $C_5$-$C_{12}$ heteroaryl; and $R^2$ is H, —OH, —C(=O)H, or —C(=O)OH.

In some embodiments, the electrical potential is applied; and the electrical potential is adjusted to maintain the concentration of $Pt^{II}$ species at about 95% to about 105% of the initial concentration.

In certain embodiments, electrical current is applied; and the electrical current is adjusted to maintain the concentration of $Pt^{II}$ species at about 95% to about 105% of the initial concentration.

In some embodiments, the reaction mixture is contained within a reaction vessel comprising a working electrode, and a counter electrode, and, optionally, a reference electrode.

In certain embodiments, the reaction vessel further comprises a $Pt^{II}$ sensing electrode.

In some embodiments, the reaction vessel is a flow reaction vessel.

In certain embodiments, the concentration of $Pt^{II}$ species is measured potentiometrically.

In some embodiments, the concentration of $Pt^{II}$ species is measured with a $Pt^{II}$ sensing electrode. For example, the $Pt^{II}$ sensing electrode is selected from the group consisting of a Pt foil electrode, a Pt mesh electrode, a Pt wire electrode, and a platinized Pt/$H_2$ electrode.

In certain embodiments, the working electrode is selected from the group consisting of a Pt foil electrode, a Pt mesh electrode, an Hg/$HgSO_4$ electrode, an Ag/AgCl electrode, a Pt wire electrode, a platinized Pt/$H_2$ electrode, a calomel electrode, a fluorine-doped tin oxide electrode, an indium-doped tin oxide electrode, a glassy carbon electrode, a carbon black electrode, a pyrolytic graphite electrode, a graphite electrode, a carbon nanotube electrode, and a boron-doped diamond electrode. For example, the working electrode is a Pt foil electrode.

In some embodiments, the reference electrode is selected from the group consisting of a Pt foil electrode, a Pt mesh electrode, an Hg/$HgSO_4$ electrode, an Ag/AgCl electrode, a Pt wire electrode, a platinized Pt/$H_2$ electrode, a calomel electrode, a fluorine-doped tin oxide electrode, an indium-doped tin oxide electrode, a glassy carbon electrode, a carbon black electrode, a pyrolytic graphite electrode, a graphite electrode, a carbon nanotube electrode, and a boron-doped diamond electrode. For example, the reference electrode is an Ag/AgCl electrode.

In certain embodiments, the counter electrode is selected from the group consisting of a Pt foil electrode, a Pt mesh electrode, an Hg/$HgSO_4$ electrode, an Ag/AgCl electrode, a Pt wire electrode, a platinized Pt/$H_2$ electrode, a calomel electrode, a fluorine-doped tin oxide electrode, an indium-doped tin oxide electrode, a glassy carbon electrode, a carbon black electrode, a pyrolytic graphite electrode, a graphite electrode, a carbon nanotube electrode, and a boron-doped diamond electrode. For example, the counter electrode is a Pt mesh electrode.

In some embodiments, the counter electrode is immersed in a solution of an electron acceptor. For example, the electron acceptor is a proton or vanadyl sulfate. Alternatively, the counter electrode is an oxygen-consuming electrode.

In certain embodiments, the anion is chloride, fluoride, acetate, nitrate, perchlorate, phosphate, or sulfate. For example, the anion is chloride.

In some embodiments, the chloride is a constituent of a salt selected from the group consisting of NaCl, KCl, LiCl, CsCl, RbCl, $MgCl_2$, $CaCl_2$, $BaCl_2$, $NH_4Cl$, and HCl. For example, the salt is NaCl.

In certain embodiments, the source of $Pt^{II}$ species is selected from the group consisting of $K_2PtCl_4$, $Na_2PtCl_4$, $Li_2PtCl_4$, $H_2PtCl_4$, $(NH_4)_2PtCl_4$, $K_2PtBr_4$, $Na_2PtBr_4$, $Li_2PtBr_4$, $H_2PtBr_4$, $(NH_4)_2PtBr_4$, $K_2Pt(CN)_4$, $Na_2Pt(CN)_4$, $Li_2Pt(CN)_4$, $H_2Pt(CN)_4$, $(NH_4)_2Pt(CN)_4$, $K_2PtCl_6$, $Na_2PtCl_6$, $Li_2PtCl_6$, $H_2PtCl_6$, $(NH_4)_2PtCl_6$, $Pt(NH_3)_4Cl_2$, $Pt(NH_3)_4(NO_3)_2$, $Pt(NH_3)_4(OH)_2$, $Pt(NH_3)_4Cl_4$, and $PtO_2$. For example, the source of $Pt^{II}$ species is $K_2PtCl_4$.

In some embodiments, the Bronsted acid is selected from the group consisting of $H_2SO_4$, HCl, $HNO_3$, $H_3PO_4$, $HClO_4$, and a carboxylic acid. For example, the Bronsted acid is HCl.

In certain embodiments, the temperature is about 20° C. to about 500° C. For example, the temperature is about 150° C. to about 300° C.

In some embodiments, electrical current is applied at a constant current.

In certain embodiments electrical potential is applied under constant potential conditions.

In some embodiments, the compound of formula $R^1$-$R^2$ is an alkane or a cycloalkane.

In certain embodiments, the compound of formula $R^1$-$R^2$ is methane.

In certain embodiments the compound of formula $R^1$-$R^2$ is oxidized to an alcohol. For example, the alcohol is a diol or a polyol.

EXAMPLES

Although methods and materials similar or equivalent to those described herein can be used in the practice of the present invention, suitable methods and materials are described below. The invention is further described in the following examples, which do not limit the scope of the invention described in the claims.

Chemicals and Materials

Potassium tetrachloroplatinate ($K_2PtCl_4$, 99.9% metals basis) was purchased from Strem chemicals. Sodium hexachloroplatinate hexahydrate ($Na_2PtCl_6 \cdot 6H_2O$, 31.3% Pt), platinum foil (0.025 mm thick), mesh wire (99.9% metals basis), and silver wire (1.0 mm dia., 99.999%) were purchased from Alfa Aesar. Glassy carbon disk (3 mm dia.) and platinum disk (2 mm dia.) electrodes and Hg/Hg$_2$SO$_4$ (in sat. K$_2$SO$_4$; 0.64 V vs SHE) reference electrode were purchased from CH Instruments. Fluorine-doped tin oxide (FTO) (TEC15, ~7 Ω/sq) was purchased from Hartford Glass Co. Inc. (Hartford City, Ind.). Nafion 117 (178 μm thick) and Nafion HP (20 μm thick; PTFE-reinforced) were purchased from Ion Power Inc., and polybenzimidazole membranes (55 μm thick) were purchased from PBI Performance Products Inc. Ceramic fritted glass tubes for the home-made double-junction Ag/AgCl reference electrode were purchased from Pine Instruments. Methane (UHP GR 4.0) was purchased from Airgas. All solutions were prepared with ultrapure water (Milli-Q Type 1; resistivity=18 MΩ-cm).

Electrochemical Methods

Electrochemical experiments were performed using a Biologic VMP3 or CHI760E potentiostat, with the latter showing more stable responses for high temperature experiments. Glassy carbon and platinum disk electrodes were polished successively with 1 μm, 0.3 μm, and 0.05 μm alumina slurry on a soft polishing cloth, with >5 min. of sonication in Milli-Q water in between. At room temperature, the counter compartment was separated from the working solution by a Nafion 117 (~180 μm thick) membrane and a Pt mesh was used as the counter electrode. Room temperature cyclic voltammetry and bulk electrolysis were performed under ambient conditions.

Figure 7:
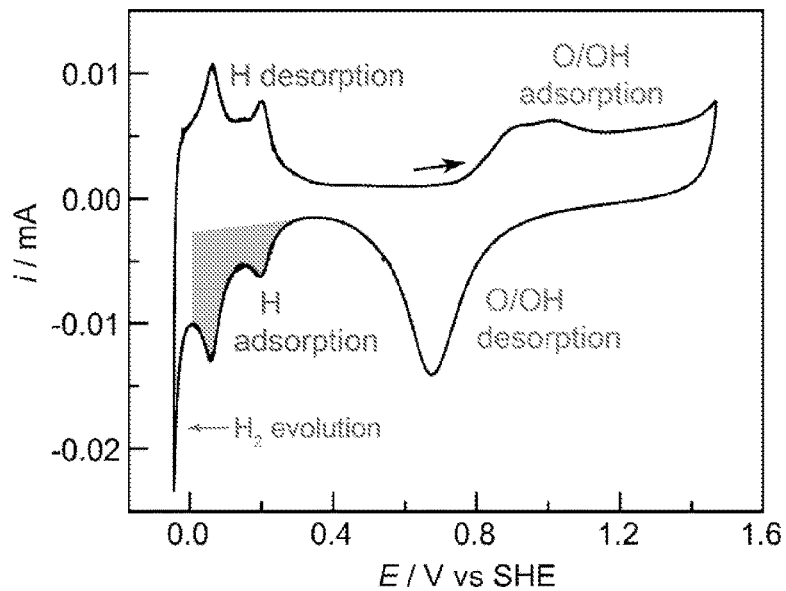
FIG. 7 depicts a cyclic voltammogram of Pt disk electrode in 0.5 M $H_2SO_4$. The H-UPD region and oxide region are marked according to conventional understanding.[1] The blue shading represents the area integrated for real surface area determination. Scan rate=100 mV s$^{-1}$.

All potential values in the manuscript are referenced to the Standard Hydrogen Electrode (SHE). Current values were reported as current densities in most cases, normalized by the surface area of the electrode. For glassy carbon and FTO electrodes, the geometric surface areas were used. For Pt electrodes, the electrochemically active surface area ("real surface area") was determined by integrating the hydrogen underpotential deposition (H-UPD) region and dividing by the known capacitance for surface-adsorbed H (210 μC/cm$^2$) (FIG. 7).

High-Temperature Electrochemistry

The reactor and its operation. A modified Parr reactor (FIG. 4) was used for high temperature (130° C.) experiments. The Parr reactor was a Series 4760 General Purpose Pressure Vessels, 300 mL size, constructed of T316 stainless steel. The reactor head was adapted with a high-pressure fitting holding PTFE-sheathed electrical wires (Conax Technologies, part no. TG-24T(KP)-A4-T), a stainless steel ⅛" needle valve for gas inlet/outlet, and a pressure relief valve (may also use a rupture disc) for safety. The connection between the electrical wires and electrodes were made by twisting the wires together and wrapping thin twisted Ti or Pt wires around them for enhanced connection. After checking the resistance values to be around 2-3 S with a multimeter, the connection was tightly wrapped with PTFE tape, which may be further heat-sealed with a flame-heated glass pipette.[27]

While omitted in the schematic diagram of the reactor (FIG. 4), the glass cell containing the working solution was actually placed in a larger glass liner that fitted snugly inside the reactor.

This was done in order to reduce the working solution volume for easier stirring and less amount of Pt salts needed. A custom-made PTFE piece was placed between the glass liner and the glass cell to fill the void space between the two and hold the working electrode, reference electrode and counter compartments in their respective positions. At the end of a high-temperature experiment, the solution volume decreased from 23 mL to 18-20 mL from evaporation and droplets of liquid condensed on the inner surfaces of the reactor. These were collected separately in the analysis (see below).

To set up the reactor, the working solution (23 mL) and counter solution were first degassed with Ar or N$_2$. After the various parts of the reactor were assembled and the reactor sealed, the headspace was purged with Ar or N$_2$ by three vacuum-refill cycles. For EMOR, the headspace was filled at room temperature with 500 psi of methane with at least three pressurization-vent cycles.

Figure 8:
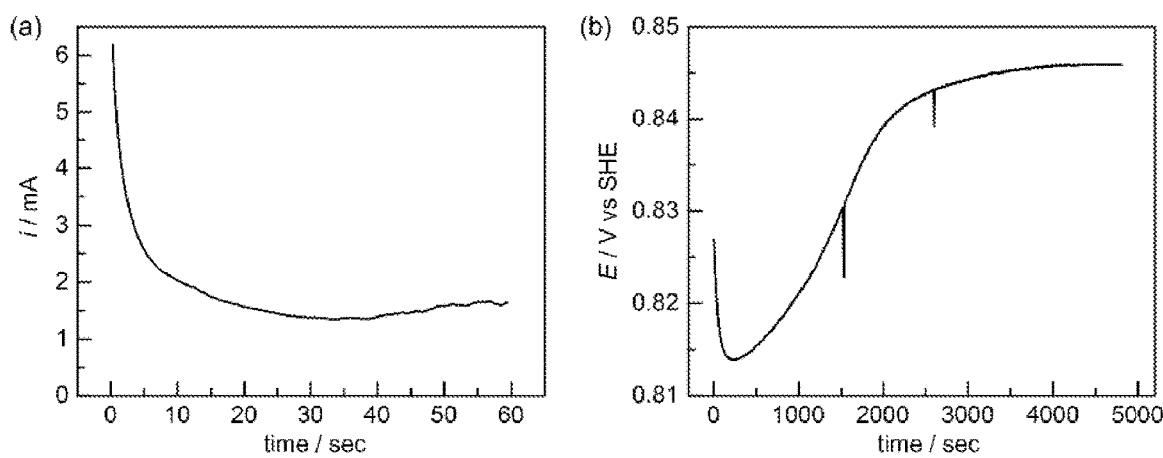
FIG. 8 depicts a current-time trace from polarization of the electrode at 1.06 V vs SHE at room temperature (stir plate is turned on ~5 sec after the start of the chronoamperometry and stir rate is increased slowly from 60 rpm to 200 rpm) (a); and an open-circuit potential registered at the electrode during heating (b). The initial rapid decrease in the OCP is because of relaxation from the previous polarization for the stir bar fidelity check shown in (a).

The solution was constantly stirred at 200 rpm with a spinfin stir bar, which has the advantage of having a relatively stationary footprint. Since the reactor walls prevented visual confirmation of effective stirring, the following procedure was used to ensure convective transport in all reactor runs: after reactor assembly and setup, the electrode was polarized at 1.06 V vs SHE and the chronoamperometric trace was recorded. Then, stirring rate was gradually increased to 200 rpm. If the current increased due to convective mass transport (e.g., FIG. 8, (a)), the application of potential was stopped, and reactor heating was started. If the current showed a smooth decay diagnostic of a quiescent solution, the reactor was disassembled to reposition the stir bar, and reassembled.

After confirming stirring, the reactor was placed in an oil bath and heated to 130° C. The actual CH$_4$ pressure during reactor operation (130° C.) is estimated at 675 psi according to the ideal gas law. During heating, the open circuit potential of the electrode was monitored and showed a steady and reproducible increase (FIG. 8, (b)). The temperature inside the reactor was considered to have stabilized when the potential reached a plateau (typically ~1 hr 20 min. after the initiation of heating), at which point applying electrochemical bias to re-oxidize Pt$^{II}$ was applied.

Figure 9:
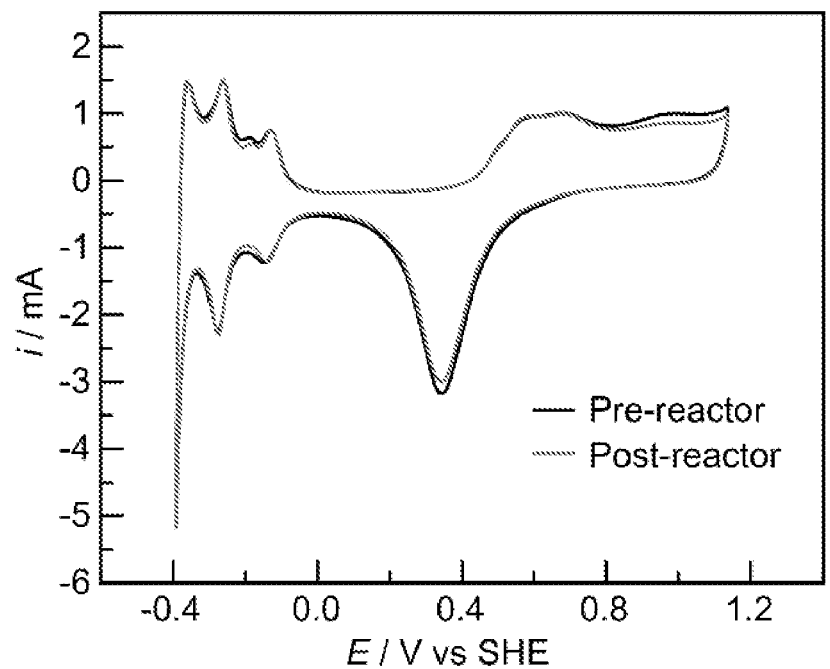
FIG. 9 depicts cyclic voltammograms of the Pt foil working electrode in 0.5 M $H_2SO_4$ before and after reactor operation for electrochemical methane oxidation reaction (EMOR). Scan rates=100 mV s$^{-1}$.

The working electrode (WE). A platinum wire or a platinum foil (for measurements of Pt$^{II}$ electro-oxidation faradaic efficiencies and EMOR) was used as the working electrode. They were cleaned before and after each experiment by several cycles of potential sweep in 0.5 M H$_2$SO$_4$ between 1.14 V and −0.4 V vs SHE until a reproducible cyclic voltammogram was obtained with characteristic hydrogen underpotential deposition and surface oxide formation features. Generally, little change was observed before and after each experiment (FIG. 9).

Figure 10:
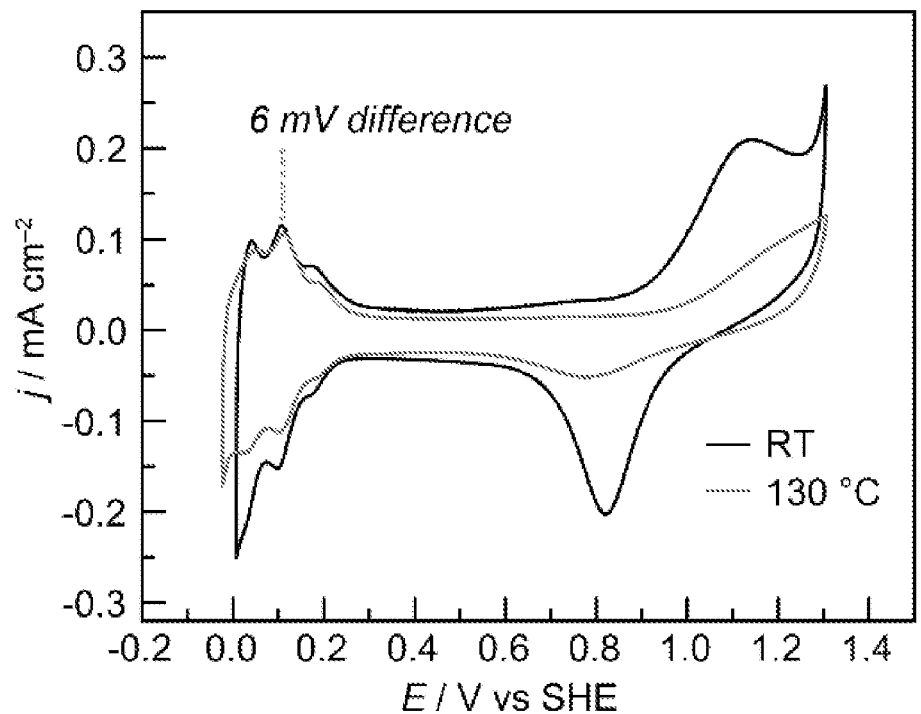
FIG. 10 depicts cyclic voltammograms of a Pt wire electrode in 0.5 M $H_2SO_4$+10 mM NaCl at room temperature and 130° C. The potentials at both temperatures were converted to SHE scale by adding 0.307 V to the recorded value.

The reference electrode (RE). For the reference electrode, a double-junction Ag/AgCl reference electrode was used. A clean silver wire (1.0 mm dia., 99.999%) was polished with fine-grit sandpaper and sonicated in 3% HNO$_3$ and Milli-Q water for 10 min. each. Then, it was galvanostatically oxidized at 10 μA/cm$^2$ for >24 hr in 0.5 M H$_2$SO$_4$ and 10 mM NaCl, with a graphite counter electrode separated from the working solution by a Nafion 117 membrane. The resulting AgCl-coated wire was encased in a glass tube closed at one end with a ceramic frit, which was encased in another larger glass tube with a ceramic frit tip. The potential of the reference electrode fabricated as such was −0.333 V vs Hg/Hg$_2$SO$_4$, or +0.307 V vs SHE at room temperature. Potentials at high temperature was also converted to the SHE scale by adding 0.307 V. While redox potential can vary with temperature,[40] it was observed that using this conversion value leads to background Pt H-UPD wave potentials that coincide between room and 130° C. data (FIG. 10), indicating that temperature dependent potential shifts may be ignored in this system. After operation at high temperature, the reference electrode typically showed a 0-3 mV variation in potential, which was ignored in the analysis of the data. After each EMOR reactor run, the AgCl-coated Ag wire was treated by application of ~5 A/cm² galvanostatic oxidation current in 0.5 M $H_2SO_4$ and 10 mM NaCl for ~30 min. to increase its longevity.

The counter electrode (CE) and counter compartment. The counter electrode was a Pt mesh separated from the working solution with $H^+$-conducting membranes. For the EMOR trials that took several hours and had considerable amount of charge passed, it was necessary to prevent the reduction of $H^+$ to $H_2$ at the counter electrode because $H_2$ was found to diffuse into the working solution and reduce the Pt ions to metallic $Pt^0$. ~3 M of vanadyl sulfate (($V^{IV}O$)($SO_4$)) was dissolved into the counter compartment electrolyte (0.5 M $H_2SO_4$ and 10 mM NaCl) to function as a surrogate electron acceptor; the blue $V^{IV}O^{2+}$ ions are reduced to $V^{III}$ ions at potentials more positive of $H^+$ reduction, thus functioning as the terminal oxidant in the system. With the vanadyl ions, no $H_2$ was detected in the headspace GC analysis.

Figure 11:
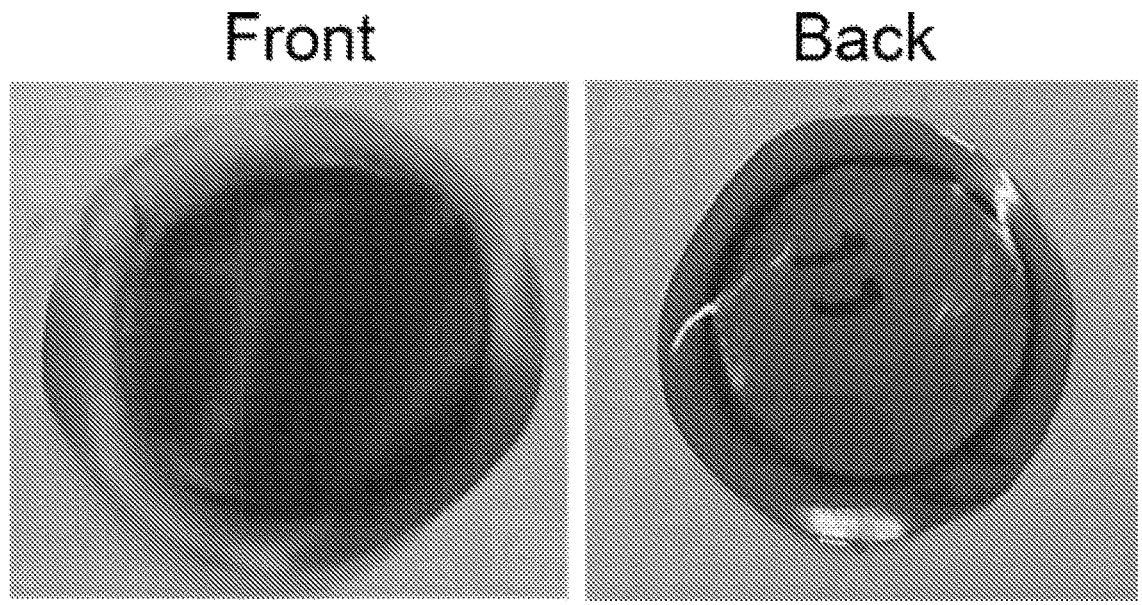
FIG. 11. depicts front and back of a polybenzimidazole membrane (first layer among five) after reactor operation for 10.5 hr. Blackened areas show $Pt^0$ deposition. The periphery, where PTFE gaskets were placed, is clear of $Pt^0$ because it was not exposed to the solution.
Figure 12:
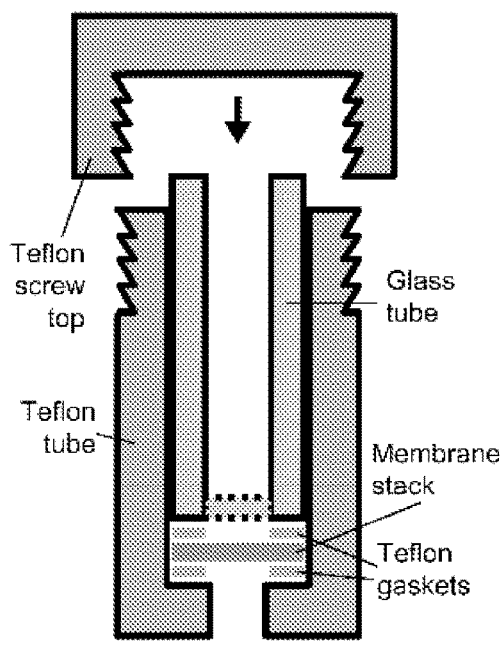
FIG. 12 depicts counter compartment design for the EMOR reactor.

As for the $H^+$-conducting membrane that separates the working and counter solutions, the temperature and presence of Pt ions necessitated the simultaneous employment of two materials. The $H^+$-conducting membrane stack consisted of alternating layers of Nafion HP (~20 m thick, PTFE-enhanced) and polybenzimidazole membranes; the Nafion is chemically stable towards Pt ions, but has a low operation temperature (up to around 80° C.). Specifically, the glass transition temperature of Nafion is 110° C.,[41] and at 130° C. loss of ionic conductivity for the thicker Nafion 117 or slow electrolyte leakage for the thinner Nafion HP was observed. On the other hand, the polybenzimidazole retains its performance at high temperature, but having aryl C—H bonds that can be activated by $Pt^{II}$, seemed to be reactive towards Pt ions so that Pt ions deposit as black $Pt^0$ on the membrane (FIG. 11). Therefore, five pairs of Nafion HP-polybenzimidazole membranes were alternatively stacked and followed by 3-4 layers of Nafion at the side facing the working solution that contains Pt ions. In order to firmly hold the membrane stack, a custom-designed apparatus was used (FIG. 12). A glass tube (wall thickness 2 mm) with a perforated glass disk on one end was snugly fitted into a PTFE tube that had a hole in the bottom. Between the bottom of the glass tube and the PTFE tube, a PTFE gasket, $H^+$-conducting membrane stack, and another PTFE gasket were placed successively. Then, to seal the edge of the membranes, the glass tube was pressed against the PTFE tube with another PTFE piece by screwing it on tightly. In this way, only the first 1-2 out of the five polybenzimidazole membranes were significantly damaged, and there was no leakage of the vanadyl ions into the working solution.

Example 1. Evaluation of $Pt^{II}$ Electro-Oxidation

Carbon electrodes. Carbon looked promising at first, as a glassy carbon electrode shows a clear electrochemical oxidation wave in the presence of $Pt^{II}$ ions (FIG. 13, (a), wave A); though the potential is quite high at first ($E_{p,a}$=1.3 V), after the first cycle, a new wave at a lower overpotential appears (wave B; $E_{p,a}$=1.0 V). When a constant potential was applied using a large surface area carbon electrode (e.g. carbon paper or carbon felt), bulk conversion of $Pt^{II}$ to $Pt^{IV}$ could be achieved, at potentials corresponding to either wave A or B. However, the net yield of $Pt^{IV}$ based on electrical charge input (i.e. the Faradaic efficiency) was on average only ~50%, and the electrode underwent a gradual deactivation (FIG. 13, (b)).

Figure 13:
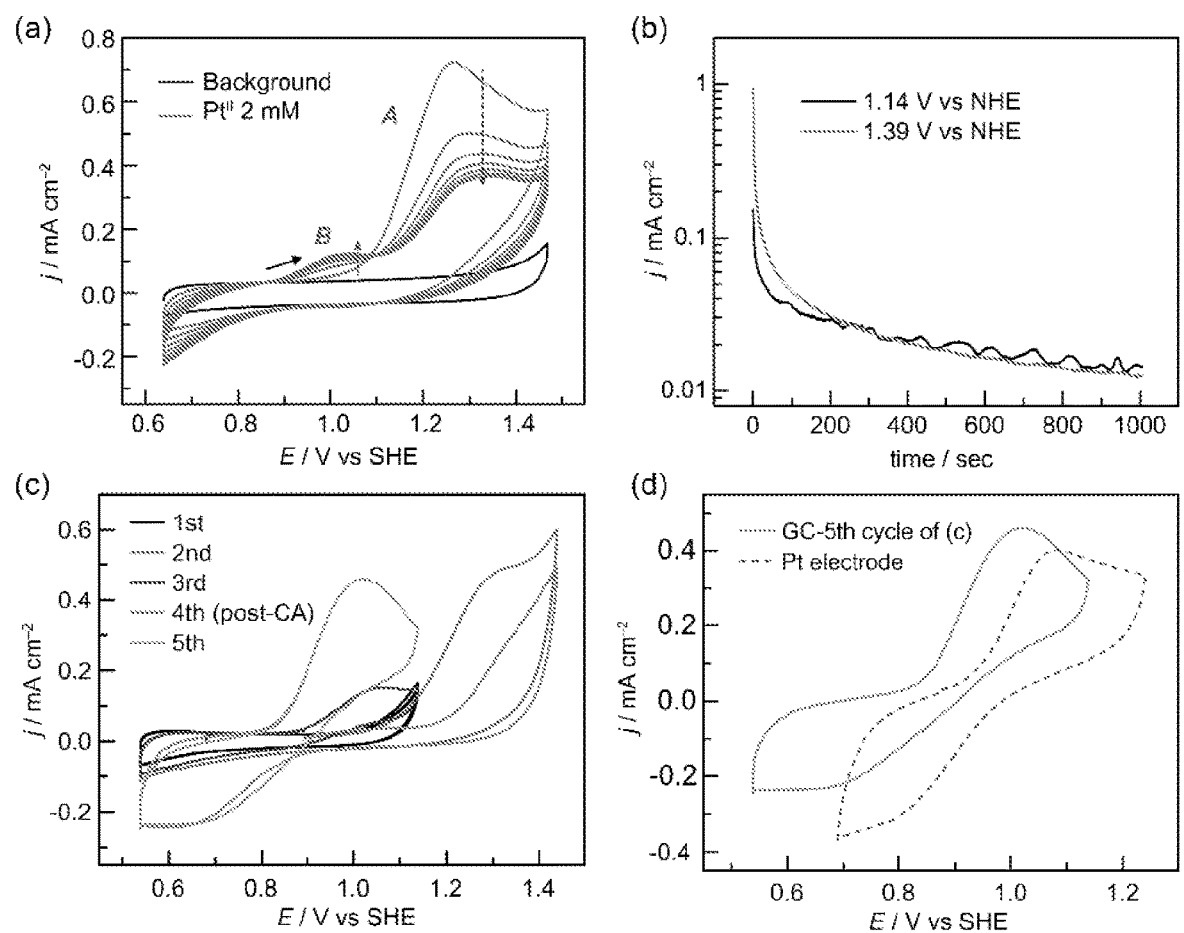
FIG. 13 depicts investigations of $Pt^{II}$ ($K_2Pt^{II}Cl_4$ in 0.5 M $H_2SO_4$) oxidation on a glassy carbon electrode. (a) Cyclic voltammograms (CV) with and without $Pt^{II}$. (b) Chronoamperometric (CA) traces at different applied potentials. The y-axis is logarithmic. (c) Series of CVs obtained on the same electrode. The 4$^{th}$ cycle was recorded after a constant-potential polarization at 1.14 V that deactivated the electrode. (d) Comparing GC and Pt electrodes. [$Pt^{II}$]=2 mM for GC and 1 mM for Pt. The currents were normalized to geometric surface area. Scan rates=100 mV/s.

In order to rationalize these observations, the following hypothesis was put forth, based on the series of CV acquired successively (FIG. 13, (c)):
(i) Wave A causes adsorption of $Pt^{IV}$ species to the electrode surface.[48] These $Pt^{IV}$ species are reduced to $Pt^0$ in the negative scan of the CV and activates the electrode for $Pt^{II}$ oxidation at a lower potential that corresponds to wave B (FIG. 13, (c), $1^{st}$ cycle vs. $3^{rd}$ cycle). In support of this hypothesis, the pair of reversible redox waves of B shows a redox potential close to that of $Pt^{II/IV}$ on Pt electrode (FIG. 13, (d)).
(ii) The surface-bound $Pt^0$ species, during constant polarization, undergoes oxidative dissolution over time and results in deactivation (FIGS. 13, (b) and (c), $4^{th}$ cycle).
(iii) It can be regenerated by re-adsorption of the $Pt^{IV}$ species and their reduction (FIG. 13, (c), $4^{th}$ & $5^{th}$ cycle).

As for the current decay at the higher potential of 1.39 V (FIG. 13, (b)), it is proposed that at such a high potential, partial oxidation of the carbon surface occurs that gradually degrades its properties as an electrode.

From the fact that deactivation was partially reversed upon negative polarization of the electrode to ~0.5 V vs SHE (FIG. 13, (c)), an attempt was made to use carbon electrodes in the EMOR reactors. However, even with periodic cathodic pulsing to regenerate the electrode activity, it was impossible to achieve sustained $Pt^{II}$-to-$Pt^{IV}$ conversion under the high-temperature/high-pressure reactor condition for methane functionalization. In hindsight, as the $Pt^{II}$ catalyst is able to activate $sp^2$ C—H bonds, functionalization of the carbon electrode surface under methane activation conditions may occur and lead to added complications. In sum, the results indicate that carbon is not a suitable electrode material for realizing electrochemical turnover of methane catalysis with $Pt^{II}$.

Figure 14:
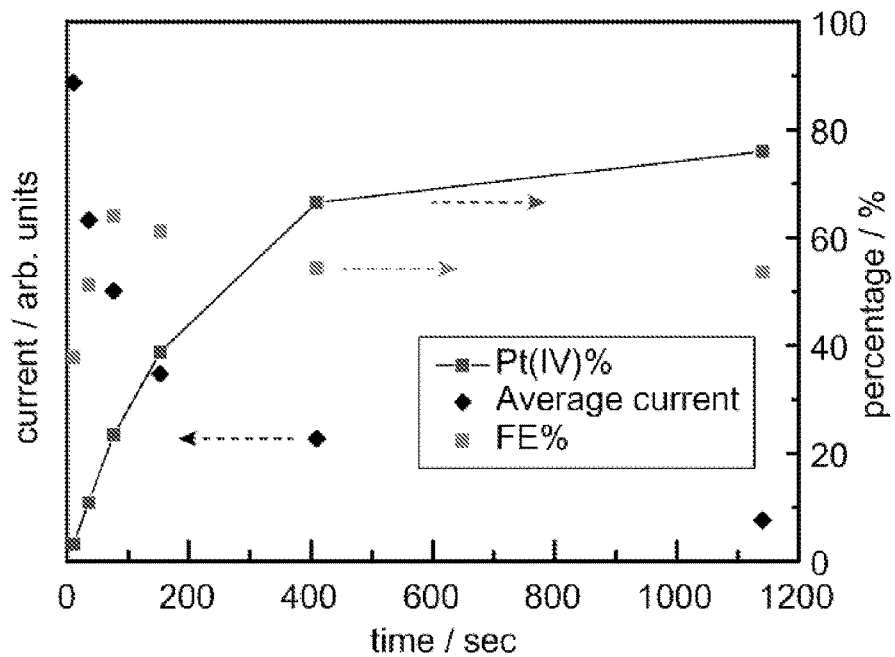
FIG. 14 depicts bulk electrolysis of a 2 mM solution of $Pt^{II}$ in 0.1 M $H_2SO_4$+10 mM NaCl on a graphite felt electrode. The solution was sampled periodically to measure the $Pt^{II}$ and $Pt^{IV}$ concentrations by UV-vis spectroscopy.
Figure 15:
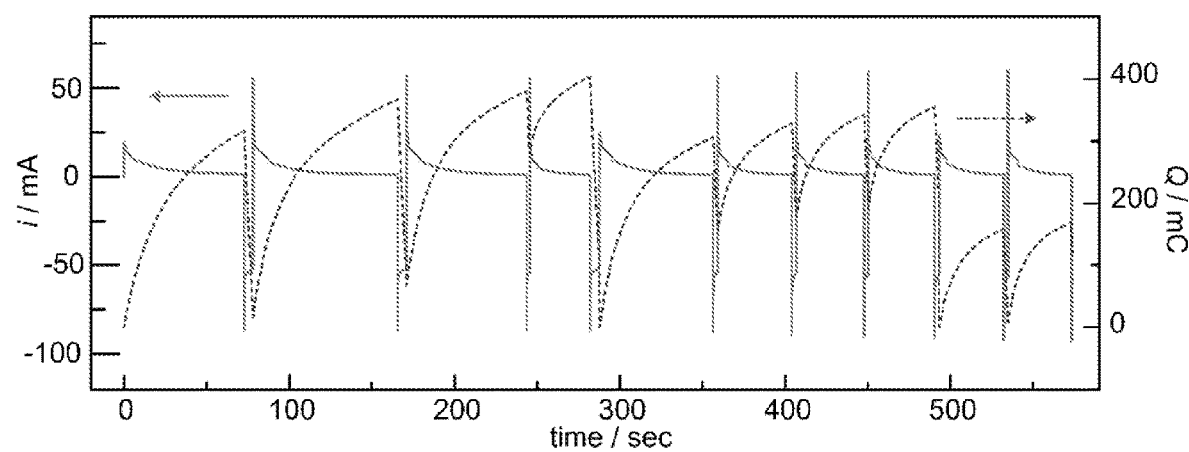
FIG. 15 depicts a portion of the current traces during EMOR reactor operation using a graphite felt working electrode (red, solid). The solution contained 0.4 mM of $Pt^{II}$ and 1.4 mM of $Pt^{IV}$ and was 12.3 mL in volume. Concentration of $Pt^{II}$ was kept to a minimum for this preliminary trial because of the low efficiency of the electrode for oxidizing $Pt^{II}$ (blue, dotted) Cumulative charge passed during the experiment. Because a lot of negative charge flowed during the cathodic polarization for electrode regeneration, it was difficult to pass a net positive charge over time (i.e. Q rises and falls in the short term, but shows no long-term increase). The post-reaction $Pt^{II}$ concentration was indicative of little $Pt^{II}$ oxidation at the electrode. For reference, the total amount of $Pt^{II}$ ions in the solution was equivalent to 474 mC.

For carbon electrodes, bulk electrolysis was also attempted. In spite of the decay in current density during oxidation, if a high-surface area carbon electrode (e.g. graphite felt or carbon paper) was used, bulk conversion of $Pt^{II}$ ions to $Pt^{IV}$ ions could be achieved (FIG. 14). However, the Faradaic efficiency (FE), which is the ratio between the amount of $Pt^{II}$ oxidized and the amount of electrical charge passed, was always ~50%. This implies the presence of parasitic oxidation process that occurs concomitantly with $Pt^{II}$ oxidation, which is likely to be some kind of oxidative degradation of the carbon electrode. Nevertheless, hopeful that $Pt^{II}$ could be converted to $Pt^{IV}$ and that electrode activity could be restored by cathodic polarization (see above), an attempt was made to force the carbon electrode to carry out $Pt^{II}$ oxidation in the high-temperature EMOR reactor with simultaneous methane oxidation. In brief, a piece of graphite felt was employed as the working electrode, and programmed the potentiostat to switch the polarization to cathodic potentials where electrode activity may be restored every time the anodic current decayed below a threshold value. Unfortunately, it was found difficult to pass a net positive charge and control the rate of $Pt^{II}$ oxidation (FIG. 15).

Figure 16:
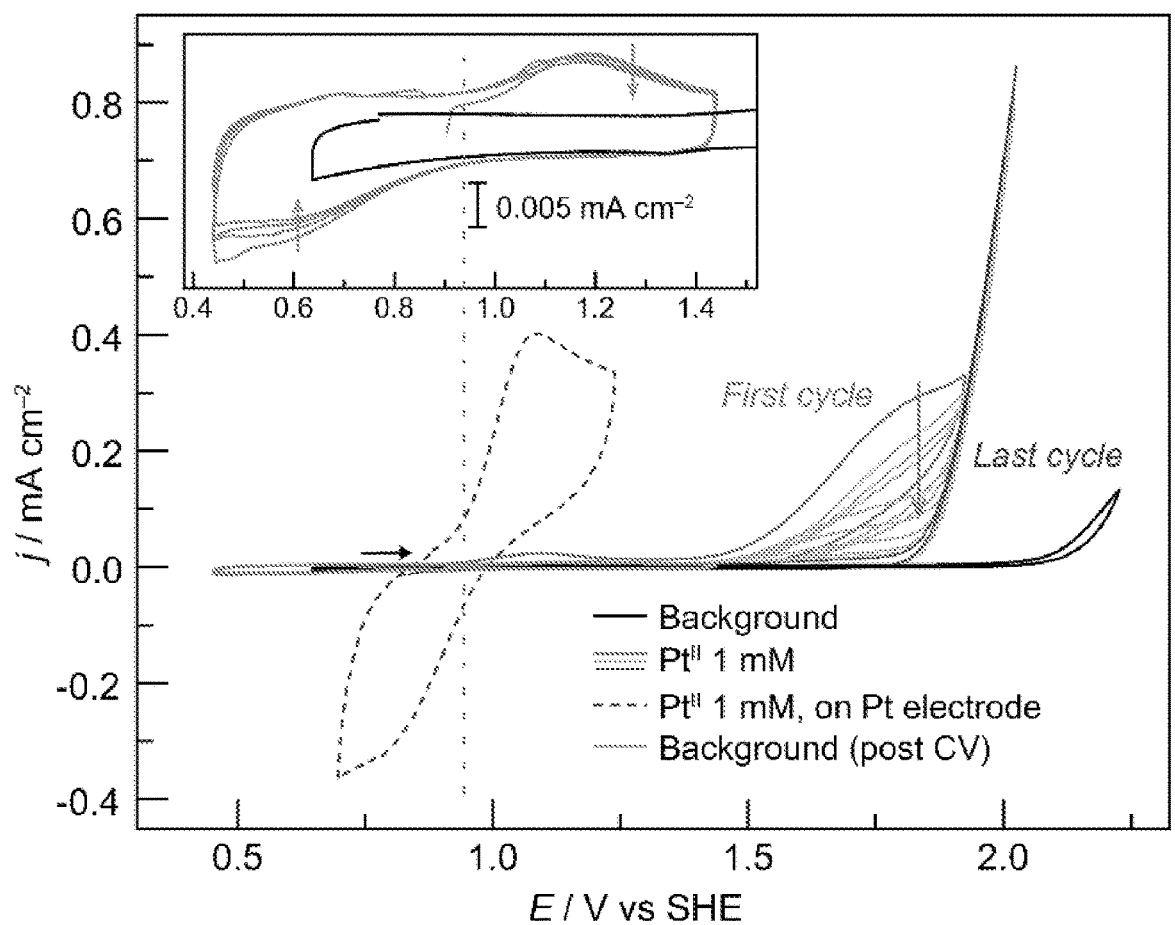
FIG. 16 depicts investigations of $Pt^{II}$ ($K_2Pt^{II}Cl_4$ in 0.5 M $H_2SO_4$ and 100 mM HCl) oxidation on a FTO electrode. CV of $Pt^{II}$ in 0.5 M $H_2SO_4$ obtained on Pt electrode (dotted blue) is shown together for comparison. The CVs of $Pt^{II}$ on FTO were acquired in the order of red-pink-brown. The green CV was obtained in blank electrolyte after recording the red-pink-brown CVs, and the inset shows magnification of this trace. The currents were all normalized to the geometric surface area for consistency. Scan rates=100 mV/s.

Fluorine-doped tin oxide (FTO) electrodes. FTO is a cheap and commonly used electrode material with optical transparency and high chemical stability. In particular, it has been shown to be remarkably robust in highly acidic and oxidizing environment.[2] Therefore, the ability of FTO to effect electrochemical oxidation of $Pt^{II}$ to $Pt^{IV}$ was investigated. As shown in FIG. 16, a $Pt^{II}$ oxidation wave can be observed at a high potential, and a catalytic water- or $Cl^-$-oxidation wave. However, the $Pt^{II}$ electro-oxidation activity quickly decayed upon several cycles (FIG. 16, red-pink-brown), though the catalytic water- or Cl⁻-oxidation remained robust (indeed, trace metal ions adsorbed on FTO have been found to be effective water oxidation electrocatalysts[49]). Interestingly, when the electrode was rinsed and transferred to a blank electrolyte, a new redox couple appeared at potentials similar to a $Pt^{II}$ couple on a Pt electrode (FIG. 16, green). It is postulated that some Pt ions have adsorbed to the electrode surface during its exposure to $Pt^{II}$ and electrochemical polarization. This redox feature slowly diminished upon repeated cycling. The CVs shown in FIG. 16 were collected in the presence of 100 mM of Cl⁻ in an effort to facilitate $Pt^{II}$ oxidation; similar results were obtained in the absence of Cl⁻.

Pt Electrodes. Additional Information for the Interpretation of $Pt^{II}$ CVs.

Figure 17:
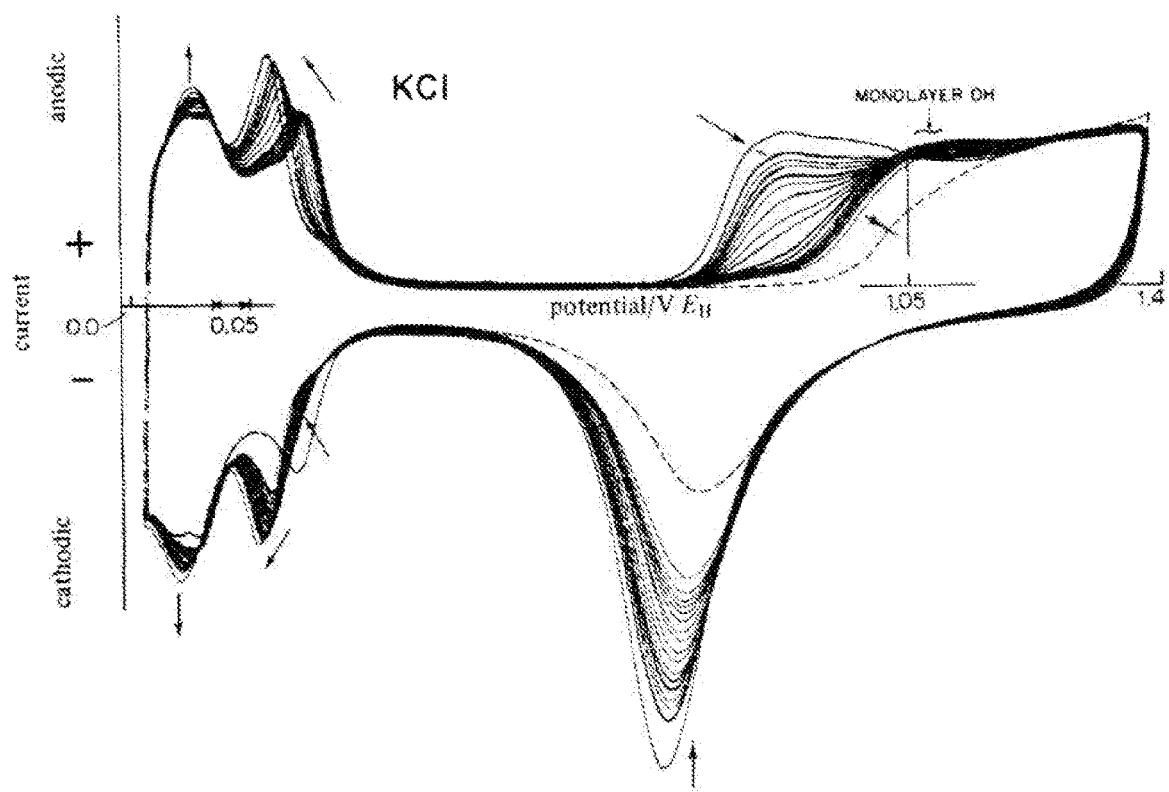
FIG. 17 depicts series of superimposed cyclic voltammograms obtained on a Pt electrode in 0.1 M $H_2SO_4$ with successive additions of Cl$^-$ ion from 10$^{-7}$ to 10$^{-5}$ M. The potential scale is versus $E_H$, the potential of the reversible hydrogen electrode (−0.059 V vs. SHE in 0.1 M $H_2SO_4$). Note the monolayer OH coverage at Pt arises at ca. 1.1 V $E_H$, close to where isopotential point occurs. Scan rate=0.060 V s$^{-1}$; $V_A$=1.375 V; T=298 K. Arrows show directions of change of curves with increasing [Cl$^-$]. Dashed curve shows continuing blocking of surface oxide beyond isopotential point for $C_{Cl^-}$>10$^{-4.5}$ M. Potential is vs. RHE. Reproduced from Ref.[33] with permission from The Royal Society of Chemistry.

Is the amount of dissociated Cl⁻ enough to suppress oxide formation? The $Pt^{II}Cl_4^{2-}$ ion undergoes slow acid hydrolysis in aqueous solutions with a rate constant of $4 \times 10^{-5}$ s⁻¹.[0.5] Therefore, after 5 min., a freshly prepared 1 mM $K_2Pt^{II}Cl_4$ solution will have generated 0.01 mM Cl⁻, and after an hour, 0.13 mM. Such a small concentration of Cl⁻ turns out to be enough to suppress oxide formation, especially at lower potentials (FIG. 17).[33]

Suppression of $Pt^{IV}$ reduction in the presence of 10 mM Cl⁻. It has been argued above, from the suppression of oxide formation, that the surface of Pt electrode adsorbs Cl⁻ from hydrolysis of the $Pt^{II}Cl_4^{2-}$ ions even without additional Cl⁻ ions. However, the $Pt^{IV}$ reduction wave was suppressed only when more Cl⁻ was added. This is because Cl⁻ adsorption depends on the electrode potential. The Cl⁻ adsorption isotherm determined with radioactive Cl⁻ (FIG. 18, (a)) shows that the isotherm is almost saturated at 0.8 V vs SHE, which is the peak potential at which $Pt^{IV}$ reduction was observed (FIG. 2, (a)). Since this isotherm was collected at 2 mM Cl⁻, it is reasonable to expect the surface coverage of Cl⁻ to be incomplete with no additional Cl⁻ yet complete at 10 mM Cl⁻ so as to exhibit the observed blocking effect towards $Pt^{IV}$ electro-reduction.

Figure 18:
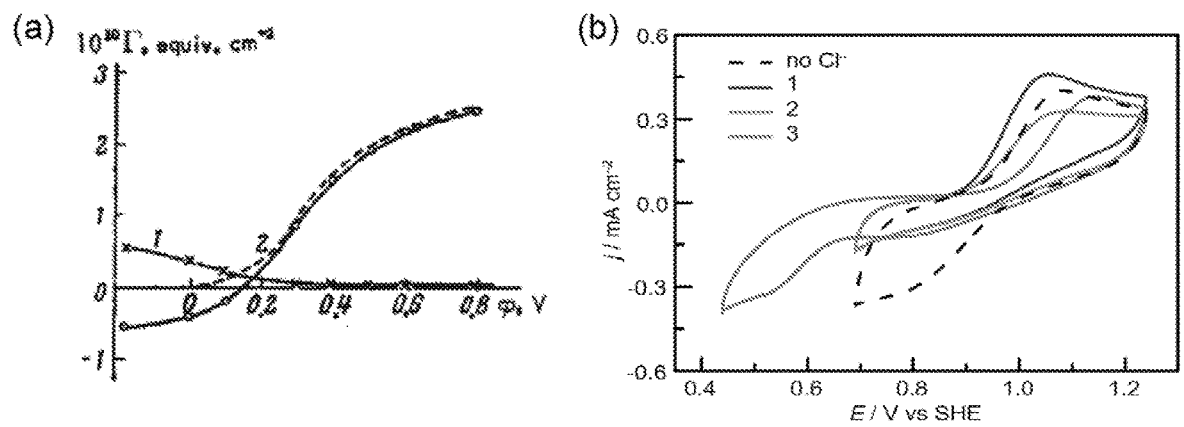
FIG. 18 depicts variation of the quantities of adsorbed Na$^+$, Cl$^-$, and H$^+$ with potential (a) (original solution was 1×10$^{-3}$ N NaCl+1×10$^{-3}$ N HCl. Adapted from reference[58]); and (cyclic voltammograms obtained on a Pt disk electrode in 1 mM $K_2Pt^{II}Cl_4$+10 mM NaCl+0.5 M $H_2SO_4$ (b). The dotted CV was obtained in a solution without the additional NaCl. The colored CVs were all acquired on the same electrode without polishing in between. They are shown here in the order they were acquired, and there were additional scans in between 2-3 in these potential windows. The decrease in $Pt^{II}$ oxidation current in the second cycle (blue vs. green) is due to mass transport limitation; that is, the absence of $Pt^{IV}$ back-reduction in the cathodic scan leads to depletion of $Pt^{II}$ in the double layer and lower oxidation current in the subsequent scan. Scan rates=100 mV/s.

As a side note, $Pt^{IV}$ reduction was observed if more negative potentials were reached (FIG. 18, (b), red), probably due to the reduced Cl⁻ coverage at the lower potentials. However, the electrode seemed to undergo some change at these very low potentials, as the peak potential for $Pt^{II}$ oxidation shifts positively afterwards. Since the thermodynamic redox potentials for $Pt^{II}/Pt^0$, $Pt^{IV}/Pt^{II}$, and $Pt^{IV}/Pt^0$ are all similar to each other ($E^0 = 0.68$-$0.76$ V vs SHE for $Pt^{IV}/Pt^{II}$, $Pt^{II}/Pt^0$, and $Pt^{IV}/Pt^0$),[29] metallic Pt may be deposited at these potentials from the Pt ions onto the electrode. If the freshly deposited $Pt^0$ has a different structure (e.g. crystallographic facet) from the electrode, it could show different electrode kinetics. After electrochemical polishing of the electrode in the blank sulfuric acid electrolyte, the $Pt^{II}$ oxidation peak returned to the initial position.

Example 2. Blocking Effect of the Surface Oxide at High Potentials

Figure 19:
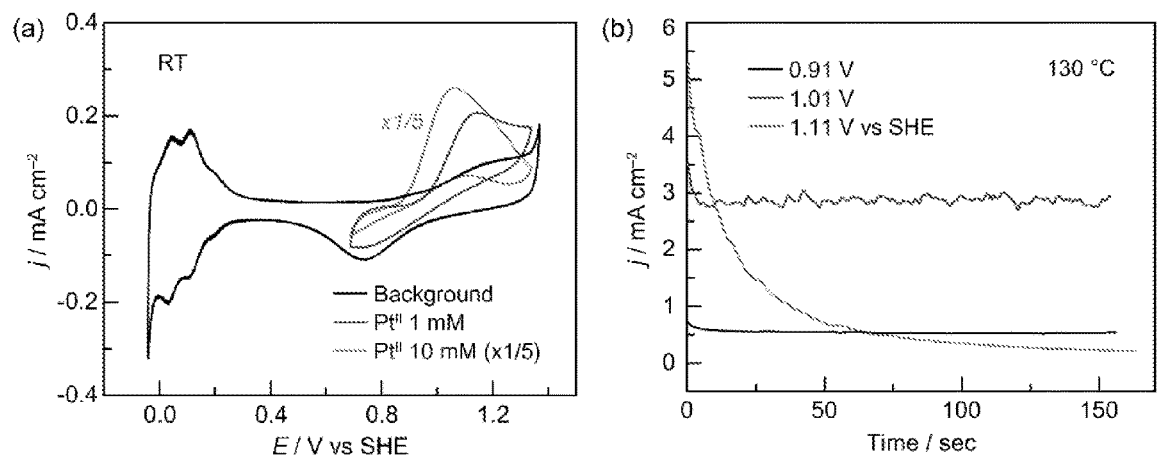
FIG. 19 depicts (a) cyclic voltammograms obtained on a Pt disk electrode in $N_2$-purged solutions containing 0, 1, and 10 mM $K_2Pt^{II}Cl_4$ in 10 mM NaCl+0.5 M $H_2SO_4$ electrolyte. Scan rates=100 mV/s. The CV of 10 mM $Pt^{II}$ is plotted at 5-fold reduced current density to match the vertical scale. Incidentally, current should be proportional to concentration of the reactant, but electrode deactivation reduced the current density at the potential where the CV of 1 mM $Pt^{II}$ shows a peak. (b) Chronoamperometric traces obtained on a Pt wire electrode at 130° C. in a stirred (500 rpm) solution of 10 mM of $K_2Pt^{II}Cl_4$ in 0.5 M $H_2SO_4$+10 mM NaCl. The current densities are normalized by the electrochemically active surface area.

While Cl⁻ ions adsorb to Pt electrodes and suppress oxide formation, at high potentials (above 1.1 V vs RHE) oxide formation resumes (FIG. 17) and the electrode surface acquires adsorbed O and/or OH species. Since $Pt^{II}$ oxidation is facilitated via a Cl-bridged inner-sphere electron transfer mechanism, such an oxide layer suppresses $Pt^{II}$ oxidation. However, in practice, such suppression in the cyclic voltammogram is observed only at high $Pt^{II}$ concentration (FIG. 19(a), blue vs red). This is because at low $[Pt^{II}]$, the limiting current density for $Pt^{II}$ oxidation (i.e. mass transport-controlled $Pt^{II}$ oxidation current) is also low; hence, there are enough open sites on the electrode despite partial coverage by the oxide. At higher $[Pt^{II}]$ where the flux of $Pt^{II}$ ions coming to the electrode is greater, the open sites on the electrode become saturated and suppression in the CV is observed. At higher temperature, the CV shows more pronounced suppression both because the flux of $Pt^{II}$ ions is greater and because the oxide layer forms faster (hence, more oxide coverage of the electrode surface at the potential where $Pt^{II}$ is oxidized). When the electrode is polarized at 1.11 V, which is above the potential at which oxide formation starts, a progressive passivation of the electrode is observed (FIG. 19, (b), red).

Figure 20:
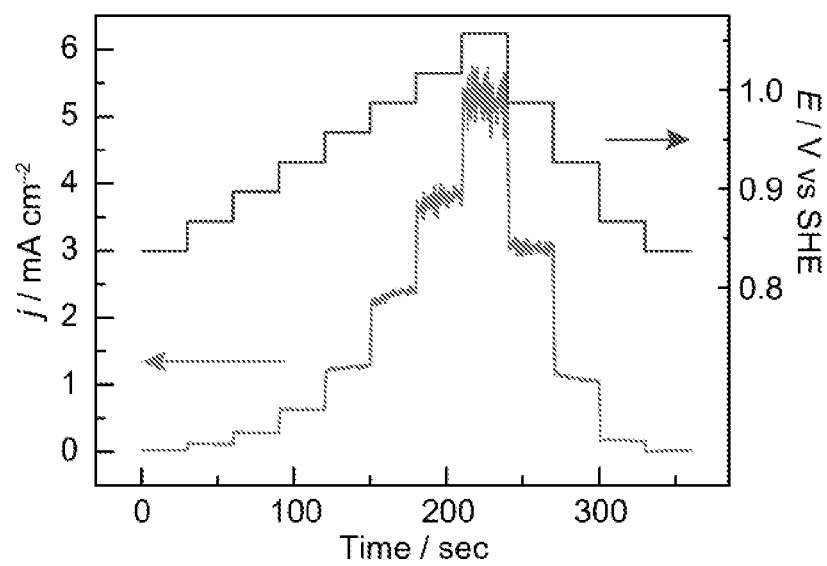
FIG. 20 depicts current recorded at different potentials on a Pt wire electrode at 130° C. for the acquisition of a Tafel plot. Solution contained 5 mM of $Pt^{II}$ and 5 mM of $Pt^{IV}$ in 0.5 M $H_2SO_4$, 10 mM NaCl.

Acquisition of current-overpotential relationship (Tafel plot). The raw data for the Tafel plot is shown in FIG. 20. In brief, the potential was varied for every 30 seconds. The current value for each potential was obtained by averaging the values over the last 5 seconds.

Assessment of $Pt^0$-catalyzed non-electrochemical oxidation of $CH_3OH$. FIG. 2, (d) highlights that Pt electrodes, which are good methanol electro-oxidation catalysts, are passivated towards electrochemical $CH_3OH$ oxidation by surface-adsorbed chloride. However, metallic Pt is also known to catalyze the non-electrochemical oxidation of $CH_3OH$ in the presence of oxidants.[38] As $Pt^{II}$ and $Pt^{IV}$ ions possess sufficient oxidizing power ($E^0 = 0.68$-$0.76$ V vs SHE for $Pt^{IV}/Pt^{II}$, $Pt^{II}/Pt^0$, and $Pt^{IV}/Pt^0$),[15] the Pt working electrode may effect non-Faradaic oxidation of methanol during EMOR. The importance of such processes was evaluated by heating 8 mM of $CH_3OH$ with 2 mM $Pt^{II}$ and 8 mM $Pt^{IV}$ in 0.5 M $H_2SO_4$ + 10 mM Cl⁻ solutions along with pieces of metallic Pt in glass ampules. The concentrations of $Pt^{II/IV}$ and Cl⁻ ions and the size of the Pt pieces were chosen to match the concentrations and working electrode surface area used in the EMOR reactors. In detail, the EMOR trials were carried out with 23 mL of working solution and a Pt foil working electrode whose electrochemically active surface area was measured to be 10.3 cm². The ampules contained 0.9 mL of the test solution. Thus, to match the ratio of Pt surface area to solution volume, the surface area of metallic Pt pieces in the ampules had to be 0.4 cm² (0.4/0.9=10.3/23). These were prepared by measuring the electrochemically active surface area of a long Pt wire in 0.5 M $H_2SO_4$, then cutting them to pieces that would be approximately 0.4 cm².

To account for oxidation of $CH_3OH$ catalyzed by $Pt^{II}$ alone, control experiments were performed in parallel with ampules that do not contain the metallic Pt pieces. Following 3 hours at 130° C., 2.8±0.2 mM $CH_3OH$ was oxidized in the presence of Pt metal, whereas the same amount, 2.7±0.4 mM, was oxidized in the absence of metallic Pt. Therefore, it was concluded that Faradaic or non-Faradaic overoxidation of the methanol product is negligible on Pt electrodes during EMOR.

Example 3. Effect of the Concentrations of $H_2SO_4$ and Cl⁻ on the Catalytic C—H Oxidation Activity of $Pt^{II}$ In order to select the electrolyte environment for carrying out the proposed EMOR, the effect of electrolyte composition on the catalytic activity of $Pt^{II}$ for methane oxidation and undesired methanol oxidation was explored.

Figure 21:
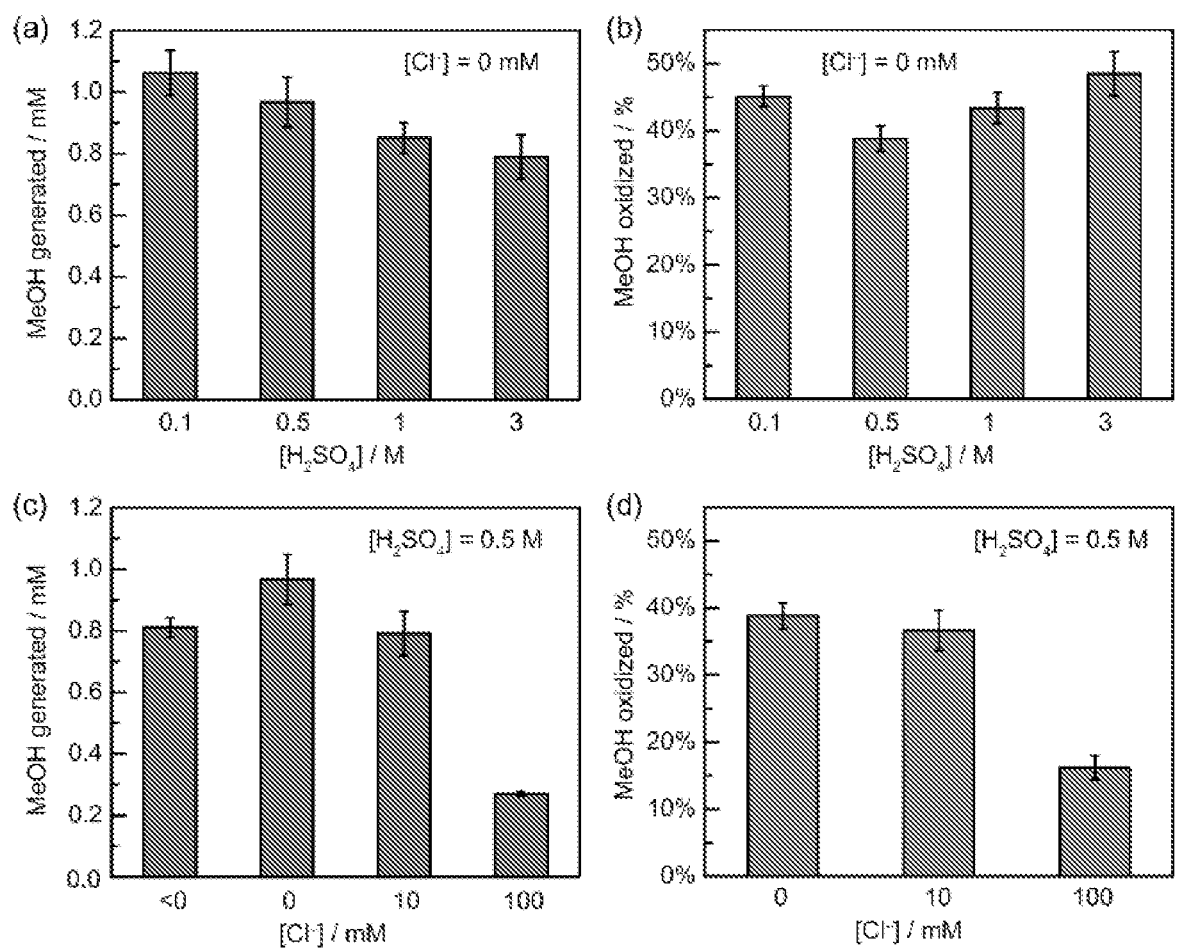
FIG. 21 depicts measurement of (a, c) methane functionalization and (b, d) methanol oxidation activities under different concentrations of (a, b) $H_2SO_4$ and (c, d) Cl$^-$. Catalyst and oxidant loadings were [$Pt^{II}$]=3 mM and [$Pt^{IV}$]=7 mM. Solutions were heated to 130° C. for 1.5 hr for (a, c) methane functionalization and 3 hr for (b, d) methanol oxidation tests. Each bar represents ≥3 sets of measurement.

Choice of acid and the effect of its concentration. The pH of the solution should be acidic in order to prevent hydrolytic degradation of the platinum ions at elevated temperatures, unless there is a high concentration of Cl⁻.[30] Conveniently, the low pH requirement (i.e. high concentration of $H_3O^+$ ions and conjugate base anions) automatically makes the solution electrically conductive, which is a prerequisite for electrochemistry. Sulfuric acid was chosen as in many other works because it is chemically very stable and low-cost, and are expected to interfere minimally with the C—H activation step of $Pt^{II}$.[51] The concentration of sulfuric acid showed a small yet measurable effect on the rate of $Pt^{II}$-catalyzed oxidation of methane to methanol and further oxidation of methanol (FIG. 21, (a) and (b)). The rate of methane oxidation decreased monotonically with increasing acid strength, which is reasonable as protonolysis of the $Pt^{II}$—$CH_3$ species competes with the subsequent steps in the catalytic cycle (FIG. 1 top). However, intriguingly, the rate of methanol oxidation showed a minimum at 0.5 M $H_2SO_4$ and increased in higher acid concentrations, which is intriguing as the protonation of $CH_3OH$ under high acid concentration usually deactivates it further by decreasing the electronic density at the C—H bond.[52] Based on previous literature, it was postulated that (i) for the $Pt^{II}$ catalyst the protonated methanol ($CH_3OH_2^+$) substrate does not have a lower reactivity compared to $CH_3OH$ because C—H activation at $Pt^{II}$ is both electrophilic and nucleophilic,[53,54] and that (ii) for the oxidation of $CH_3OH_2^+$, the $Pt^{II}Cl_3(H_2O)^-$ species, which is higher in concentration but less reactive than $Pt^{II}Cl_2(H_2O)_2$ for oxidation of $CH_3OH$, is more active than $Pt^{II}Cl_2(H_2O)_2$ because the transition state is charge-neutral.[51,55]

Effect of chloride concentration. The presented data highlight that $Cl^-$ is essential for inhibiting $CH_3OH$ oxidation at the Pt surface. However, $Cl^-$ ions are also known to inhibit the C—H activation step in FIG. 1.[54] Among the different species of $Pt^{II}$ ions in the solution (i.e. $[PtCl_x(H_2O)_{(4-x)}]^{(2-x)}$), the rate of H/D exchange of cyclohexane at $Pt^{II}$ is the fastest at the neutral $Pt^{II}Cl_2(H_2O)_2$ ion.[54,55] Hence, $Cl^-$ is known to inhibit the C—H activation step by decreasing the equilibrium fraction of $Pt^{II}Cl_2(H_2O)_2$.

Therefore, initially (before the information about electrode passivation by $Cl^-$ was obtained) attempts were made to decrease $[Cl^-]$ as much as possible by exploiting the fact that the electrochemical oxidation of $Pt^{II}$ to $Pt^{IV}$ proceeds even in the absence of extra $Cl^-$. A solution of 3 mM $Pt^{II}$ and 7 mM $Pt^{IV}$ having a net "negative" $Cl^-$ concentration was prepared by generating the $Pt^{IV}$ ions by bulk electrolysis of a solution of $K_2Pt^{II}Cl_4$ without any added $Cl^-$ (cf. $Pt^{IV}$ from $Na_2Pt^{IV}Cl_6$ has two more $Cl^-$ than $Pt^{II}$). With the expectation that this will increase the fraction of $Pt^{II}Cl_2(H_2O)_2$ among the $Pt^{II}$ ions in the solution and accelerate the overall rate for methane oxidation, the solution was tested for reaction with methane. Surprisingly, this solution actually showed slower production of methanol compared to a solution containing equal concentrations of $Pt^{II}$ and $Pt^{IV}$ but $Pt^{IV}Cl_6^{2-}$ as the $Pt^{IV}$ ions (FIG. 21, (c)). This could be due to the reduced efficacy of the $Pt^{IV}Cl_4(H_2O)_2$ ions as oxidants compared to $Pt^{IV}Cl_6^{2-}$; if a chloride-bridged inner sphere mechanism is operative as observed in self-exchange studies of $Pt^{II}(NH_3)_4^{2+}$ and $Pt^{IV}(NH_3)_4Cl_2^{2+}$, species such as $Pt^{IV}Cl_4(H_2O)_2$ may be slower to oxidize the transient $Pt^{II}(CH_3)Cl_3^{2-}$ species, though $Pt^{IV}Cl_4(H_2O)_2$ may have a higher oxidation potential.[25] Whatever the exact reason is, it was fortuitous since such a condition could not be employed in the system because $Cl^-$ is required for electrode passivation towards $CH_3OH$ oxidation.

On the other hand, adding in 10 mM of $Cl^-$ decreased the rate of methane-to-methanol conversion only slightly. The reduction in the overall rate was more pronounced at 100 mM of $Cl^-$, but was less than an inverse first order, as the rate decreased by only ~⅓ for a 10-fold increase in $[Cl^-]$; the reaction order in $Cl^-$ depends on the range of $[Cl^-]$.[55] The effect of $[Cl^-]$ on methanol oxidation (FIG. 21, (d)) was similar to that on methane oxidation. The negative order in $[Cl^-]$ is, however, expected to increase as $[Cl^-]$ is increased.[54]

Example 4. Mathematical Treatment of the Relationship Between the Applied Current and the $Pt^{II}$:$Pt^{IV}$ Ratio Given the 100% Faradaic efficiency of $Pt^{II/IV}$ oxidation at the Pt electrode, the molar rate of $Pt^{II}$ oxidation, $r_{ox}$, is directly proportional to the applied current (i):

$$r_{ox} = \frac{i}{2FV} \quad (1)$$

where F is Faraday's constant and V is the volume of the reaction solution. The denominator contains a factor of 2 to account for the two electrons required for each $Pt^{II/IV}$ oxidation reaction. The rate of methane oxidation catalysis, $r_{cat}$, is first-order in $[Pt^{II}]$:

$$r_{cat} = k_{obs}[Pt^{II}] \quad (2)$$

where $k_{obs}$ is the observed pseudo-first order rate constant under the $CH_4$ pressure and temperature conditions employed. For every catalytic turnover, an equivalent of $Pt^{IV}$ is reduced to $Pt^{II}$, and, thus, $r_{cat}$ has a positive contribution to $d[Pt^{II}]/dt$. On the other hand, $r_{ox}$ has a negative contribution to $d[Pt^{II}]/dt$. Overall, the following is obtained:

$$\frac{d[Pt^{II}]}{dt} = r_{cat} - r_{ox} \quad (3)$$

$$= k_{obs}[Pt^{II}] - r_{ox} \quad (4)$$

For a fixed value of applied current, $r_{ox}$ is time-invariant, thus integration yields:

$$[Pt^{II}] = Ce^{k_{obs}t} + r_{ox}/k_{obs} \quad (5)$$

Upon solving for the integration constant C using the initial conditions, the following is obtained:

$$[Pt^{II}] = ([Pt^{II}]_{t=0} - r_{ox}/k_{obs})e^{k_{obs}t} + r_{ox}/k_{obs} \quad (6)$$

If $r_{ox}$ exactly equals the rate of $Pt^{II}$-catalyzed C—H functionalization ($r_{ox} = k_{obs}[Pt^{II}]_{t=0}$), the time-dependent exponential term in equation 6 will go to zero and $[Pt^{II}]$ will remain constant over time. However, even very small differences between $r_{ox}$ and $k_{obs}[Pt^{II}]_{t=0}$ will result in a non-zero exponential term that will cause the $[Pt^{II}]$ and, thus, the $Pt^{II}$:$Pt^{IV}$ ratio, to rapidly deviate from its initial value over time. If $r_{ox}$ is constantly re-adjusted to match $r_{cat}$, however, $[Pt^{II}]$ can be maintained at a steady-state. Therefore, these equations highlight the need to constantly modulate the rate of $Pt^{II}$ electro-oxidation, $r_{ox}$.

Example 5. The Relationship Between Overpotential (η) and Reactor Configuration

The required η is determined by the current density (j) required for steady-state catalysis, and j equals the required current (i) divided by the electrode area (A). Since i depends on the reactor solution volume (V) and the catalytic rate constant ($k_{obs}$) (eq. 1 and 4 above), the magnitude of η will also depend on these parameters.

While enlarging A will decrease η and, thus, the electrical energy input, it will also increase electrode cost and may increase the rate of parasitic $Pt^0$-catalyzed $CH_3OH$ oxidation. It is important to underscore that in the disclosed reactors, η was quite small (<50 mV) even when the electrode was sufficiently small as to observed negligible surface-mediated $CH_3OH$ oxidation (see Assessment of $Pt^0$-catalyzed non-electrochemical oxidation of $CH_3OH$ in Section 2). Also, because the rate of $Pt^{II}$ electro-oxidation at any η is proportional to $[Pt^{II}]$, the $[Pt^{II}]$ can be increased to increase the overall rate of catalysis without requiring additional overpotential.

that without stabilizing additives, nanoparticulate $Pt^0$ coagulate and settle within a few hours so that they become visible.[56]

The amount of Pt ions that deposited as $Pt^0$ was calculated from the difference in total μmol of $Pt^{II}$ and $Pt^{IV}$ ions before and after the reaction. Dividing this by the initial μmol of Pt ions, obtain the % loss of Pt ions for each EMOR trial can be obtained, as shown in Table 2 and the concentration scale-up trial in Table 5. As shown in Table 6, the amount of the irreversible $Pt^0$ deposition increases with increasing reactor operation time. The higher concentration trial showed negligible $Pt^0$ loss, which may be due to the higher $Pt^{IV}$ concentration overall.

TABLE 5

EMOR reactor results from two trials where run duration was identical (10.5 h) but concentrations of $Pt^{II}$, $Pt^{IV}$ and $Cl^-$ differed by 5 times.

| $[Pt^{II}]$ | $i_{ave}^b$ (mA) | Final $Pt^{II}$ (%) | Product (μmol (rel. fraction)) | | | | | approx. $TON^d$ | | approx. $TOF^d$ ($hr^{-1}$) | |
| | | | $CH_3OH$ | $CH_3Cl$ | $CH_2(OH)_2$ | HCOOH | $CO_2$ | $CH_3X$ | Total | $CH_3X$ | Total |
|---|---|---|---|---|---|---|---|---|---|---|---|
| 3 | 0.88 | 19% | 93.7 (71%) | 27.9 (21%) | 5.1 (4%) | 1.2 (1%) | 4.4 (3%) | 2.7 | 3.4 | 0.26 | 0.32 |
| 15 | 2.47 | 20% | 178.9 (51%) | 131.6 (37%) | 32.6 (9%) | 3.0 (1%) | 4.9 (1%) | 1.2 | 1.5 | 0.11 | 0.15 |

Example 6. Observation of $Pt^0$ in the Reactor

Figure 22:
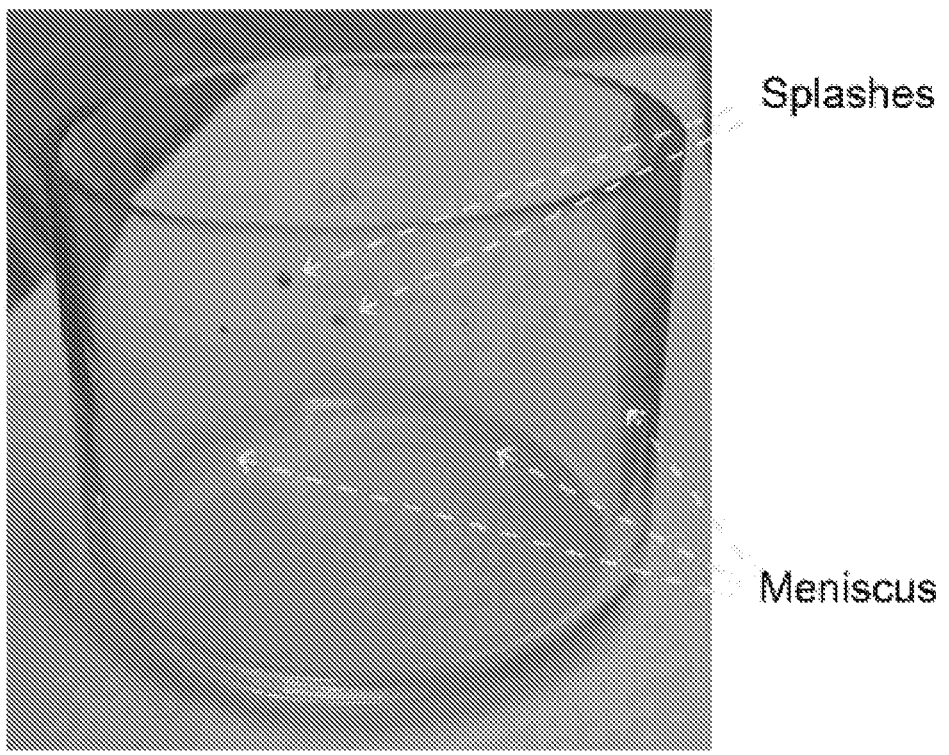
FIG. 22 is a photograph of the glass cell after a 29-hr reactor operation.

As stated above, $Pt^{II}$ decomposes to $Pt^0$ when the oxidant, $Pt^{IV}$, is depleted. In the reactors where the $Pt^{II}$:$Pt^{IV}$ ratio was constantly monitored and controlled, no $Pt^0$ was visible in the well-stirred portion of the working solution. However, in areas of poor convection, $Pt^0$ formation was observed. First, there were some specks of grey $Pt^0$ on the upper parts of the glass cell wall where droplets of the reaction solution had splashed (FIG. 22); isolated from the bulk solution in contact with the electrode, these droplets were depleted of $Pt^{IV}$ from the reaction with methane and hence deposited $Pt^0$. For long reaction times, a faint line of grey $Pt^0$ was also observed along the meniscus of the reaction solution (FIG. 22). Because the hydrophilic surface of aqua regia cleaned glass cell wall draws up the solution to form a highly concave meniscus, and because the solution was stirred rather gently (200 rpm) to avoid bubble formation that could block the solution channel between the working and counter compartments, it is assumed that the thin layer of solution in contact with the glass wall at the meniscus may have been stagnant, resulting in $Pt^{IV}$ depletion and $Pt^0$ deposition. The narrow crevice between the $H^+$-conducting membranes and the PTFE block encasing the counter compartment also accumulated $Pt^0$ over time, which is believed to be also due to the slow mass transport and depletion of $Pt^{IV}$ in that constricted space. Lastly, as mentioned earlier, $Pt^0$ deposition was found on/inside the $H^+$-conducting membranes (FIG. 11). This is attributed to the slow leakage of Pt ions through the thin Nafion HP membrane (~20 m) and their reaction with the polybenzimidazole membrane. It is important to emphasize that there was no visible $Pt^0$ in the well-stirred part of the solution where $Pt^{IV}$ replenishment through mass transport was unhindered, demonstrating the importance of maintaining an appropriate $Pt^{II}$:$Pt^{IV}$ ratio. In comparison, if a solution of $Pt^{II}$ and $Pt^{IV}$ is reacted with methane without concomitant electrochemical oxidation, visible chunks of $Pt^0$ are formed and float around in the bulk of the solution. It is also known

TABLE 6

Amount of $Pt^0$ deposition from reactor operations of varying time duration.

| Time (hr) | Pt loss as $Pt^0$ |
|---|---|
| 4.9 | 3.0% |
| 10.5 | 4.4% |
| 18.4 | 6.5% |
| 29.3 | 13% |
| 10.5 (5x concentrations) | 0.0% |

Figure 23:
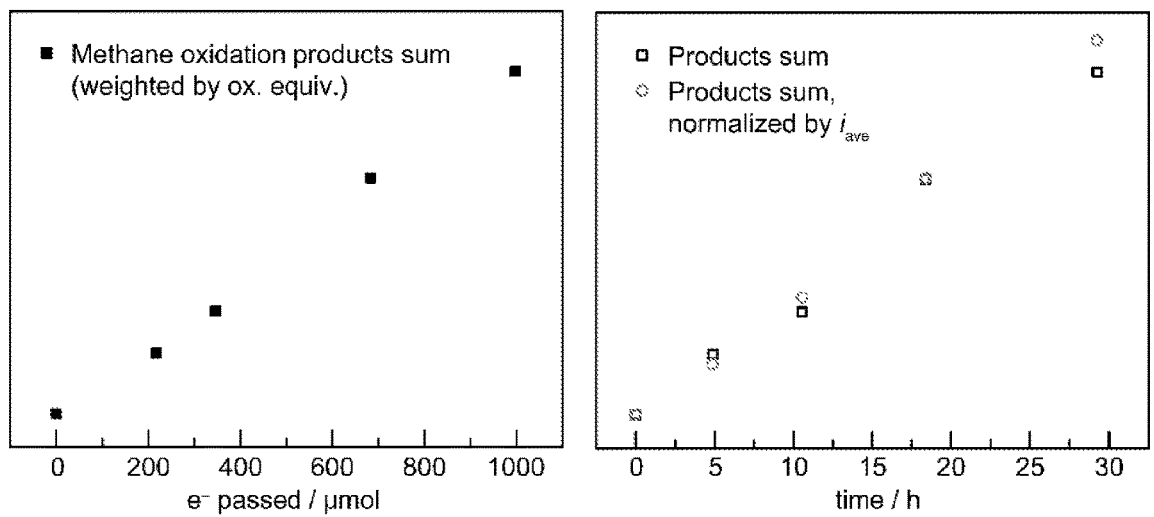
FIG. 23 depicts the total amount of methane oxidation products from the four EMOR trials (Table 2) plotted against (left) the amount of charge passed and (right) the reaction time. The product amount was calculated in a way that counted the total number of oxidation events ($\mu mol_{TotalProduct}=\mu mol_{CH3OH}+\mu mol_{CH3Cl}+2*\mu mol_{CH2(OH)2}+3*\mu mol_{HCOOH}+4*\mu mol_{CO2}$). When the product amount is plotted against reaction time (right, hollow black squares), the trend is less linear because of variation in the amount of charge passed per time between EMOR trials. Normalization by $i_{ave}$ makes the plot more linear (right, hollow red circles).

Explanation for normalization of product concentration by $i_{ave}$ in FIG. 5, (a). Since electrochemical oxidation provides the oxidizing equivalents, a linear correlation exists between the total methane oxidation products and the charge passed (FIG. 23, left). If the electric current (i), which is by definition charge passed per time, is constant throughout the EMOR, a linear correlation will also arise between methane oxidation products and time. However, because of constant modulation of i with minor fluctuations in $[Pt^{II}]$, i is not constant. Indeed, if the product is plotted versus time, the plot becomes skewed (FIG. 23, right, black squares). Therefore, the amount of product is normalized by the average current of each EMOR trial, which gives a much more linear correlation between the amount of product and reaction time (FIG. 23, right, red circles). Product amounts in μmol were converted to concentration (mM) by dividing by the reaction solution volume, 23 mL.

Concentration scale-up trial. All of the EMOR reactor experiments reported in this disclosure were done with identical reaction solution composition ($[Pt^{II}]$=3 mM, $[Pt^{IV}]$=7 mM, $[Cl^-]$=10 mM). In order to gain further understanding of the system, it was attempted to scale up the concentrations of all species ($Pt^{II}$, $Pt^{IV}$ and $Cl^-$) by 5 times. The reactor was run for 10.5 hr for straightforward comparison with a reactor run for the same length of time with the default concentrations. The result is shown in Table 5, and here are some differences that were observed for the higher concentration trial:

(i) The overall rate of catalysis ($r_{cat}$) increased thanks to the increased $Pt^{II}$ concentration (compare product µmols and $i_{ave}$'s). The increase was not 5-fold but rather ~2.5-fold because of the inhibitory effect of $Cl^-$, which is reflected in the ~2-fold reduction in TON and TOF.

(ii) Due to the higher $Cl^-$ concentration, more $CH_3Cl$ and less $CH_3OH$ were formed.

(iii) The fraction of $CO_2$ was lower even though the reactor was run for the same amount of time and generated higher $CH_3OH$ concentration. In combination with the fourth observation (negligible $Pt^0$ deposition), this observation supports the hypothesis set forth in Section 6, that further oxidation of $CH_2(OH)_2$ and HCOOH inside the EMOR reactor may have been catalyzed by $Pt^0$.

(iv) There was almost no loss of Pt ions as $Pt^0$, presumably due to a higher concentration of $Pt^{IV}$ (see above).

Example 7. Simulation of Reactions in the EMOR Reactor

Simulation details. The concentrations of various methane oxidation products were calculated numerically with the simple mechanism in FIG. 5, (b) using Microsoft Excel. For example, for $CH_3OH$, $$\frac{d[CH_3OH]}{dt} = k_1[CH_4] - k_2[CH_3OH] + k_4[CH_3Cl]$$

$$[CH_3OH]_{t+1} = [CH_3OH]_t + k_1[CH_4]\Delta t - k_2[CH_3OH]_t\Delta t + k_6[CH_3Cl]_t\Delta t$$

and for $CH_2(OH)_2$, $$\frac{d[CH_2(OH)_2]}{dt} = k_2[CH_3OH] - k_3[CH_2(OH)_2]$$

$$[CH_2(OH)_2]_{t+1} = [CH_2(OH)_2]_t + k_2[CH_3OH]_t\Delta t - k_3[CH_2(OH)_2]_t\Delta t$$

$\Delta t$ was set to 0.0093 hr, a sufficiently small value that showed no difference in the simulation when it was increased or decreased. With the given pressure and temperature, [CH$_4$] was set to 44 mM.[57] This is an approximate value because the equation for calculating Henry's constant at different temperatures was only validated in the range T=273-361 K, while the reactor was run at 403 K. $P_{CH4}$ and [CH$_4$] was considered to be constant throughout the reactor run because the amount of methane that was converted to products in the EMOR reactors (<400 µmol for the longest reactor run) was negligible compared to the amount of methane in the large headspace (~200 mmol). Then, the parameters $k_1$-$k_6$ were adjusted until a good fit with experimental reactor data was achieved. The fitted parameters are given in Table 4. To emphasize, the fitted parameters are not true rate constants but apparent values, and that they are crude estimations as the data-to-parameter ratio is low and the reaction mechanism (FIG. 5, (b)) was not rigorously validated. Nonetheless, these serve as a useful approximation of the reactions occurring during EMOR.

Example 8. Independent Determination of Relative Rate Constants Outside the EMOR Reactor $CH_4$ vs. $CH_3OH$ oxidation. In the literature, there are two cases that explicitly report experimentally assessed selectivity of aqueous $Pt^{II}$ chloride salt for $CH_4$ vs $CH_3OH$ (which is not necessarily identical to the selectivity of $RCH_3$ vs $RC$ $H_2OH$). The experiments were reproduced by the inventors. The different relative rates are summarized in Table 7. Parenthetically, a model $Pt^{II}$ complex in trifluoroethanol, (N—N)$Pt^{II}$(CH$_3$)(TFE) (N—N=ArN=C(CH$_3$)—C(CH$_3$)=NAr, TFE=trifluoroethanol), showed relative rates of C—H activation of $k_{CH4}/k_{CH3OH}$=0.77.[12]

TABLE 7

Experimentally assessed relative rates of C—H oxidation of $CH_4$ and $CH_3OH$ by $Pt^{II}$ + $Pt^{IV}$.

| T (° C.) | $P_{CH4}$ (atm) | $P_{O2}$ (atm) | Duration (hr) | $k_{CH4}/k_{CH3OH}$ | Ref. |
|---|---|---|---|---|---|
| 105 | 41, 83 | 14 | >300 | 0.17[a] | 59 |
| 120 | 10 | 0 | 1 | 6 | 11 |
| 130 | 6.9 | 0 | 1.17 | 0.8-1.2 | This work |

[a]Authors mention possibility of $Pt^0$ formation during the reaction.

For the estimation experiment, two identical high-pressure NMR tubes were charged with the same solution of 3 mM $Pt^{II}$+7 mM $Pt^{IV}$ in the 0.5 M $H_2SO_4$+10 mM NaCl electrolyte. One contained 7.5 mM of $CH_3OH$ while the other did not. The tube without $CH_3OH$ (Tube 1) was pressurized with 100 psi of $CH_4$, while the tube containing $CH_3OH$ (Tube 2) was pressurized with 100 psi of Ar. Another heavy-walled NMR tube was charged with blank electrolyte containing internal standards and pressurized with 100 psi of $CH_4$ (Tube 3). The three heavy-walled NMR tubes were heated together in an oil bath for 1 hr and 10 min at 130° C., then quantitated for the amount of $CH_3OH$ and compared with the initial $CH_4$ or $CH_3OH$ concentration. The initial $CH_4$ concentration in Tube 1 was estimated from Tube 3, which showed [CH$_4$]=8.6 mM before heating and 5.7 mM after heating due to reduced solubility of methane at elevated temperatures; it is difficult to determine the exact $CH_4$ concentration in Tube 1 because the constricted geometry of the tube slows down gas/liquid equilibration. As the table shows, from 5.7-8.6 mM of methane 1.1 mM of net methanol formation was observed (13-19% of initial $CH_4$), and from 7.5 mM of methanol 1.2 mM of net oxidation was observed (16% of initial $CH_3OH$). Taking the ratio of the relative reacted amounts, $k_{CH4}/k_{CH3OH}$ is estimated to be 0.8-1.2. These results are summarized in Table 8.

TABLE 8

Concentrations of $CH_4$ and $CH_3OH$ before and after reaction with $Pt^{II}$ + $Pt^{IV}$ at 130° C.

| | Initial | Final | Reacted amount |
|---|---|---|---|
| Tube 1 | [CH$_4$] = 8.6 → 5.7 mM | [CH$_3$OH] = 1.1 mM | 1.1 mM (13-19%) |
| Tube 2 | [CH$_3$OH] = 7.5 mM | [CH$_3$OH] = 6.3 mM | 1.2 mM (16%) |

$CH_3OH$, $CH_2(OH)_2$, HCOOH oxidation. Sealed glass ampules containing solutions of $Pt^{II}$, $Pt^{IV}$ and the different substrates in 0.5 M $H_2SO_4$+10 mM NaCl electrolyte were heated at 130° C. The decrease in substrate concentrations for different time duration are compared in Table 9.

TABLE 9

Estimation of rates of substrate oxidation by $Pt^{II} + Pt^{IV}$ at 130° C.

| Substrate (=S) | $[S]_{initial}$ (mM) | Duration (hr) | $\Delta[S]/[S]_{initial}$ (%) |
|---|---|---|---|
| CH$_3$OH | 11.13 | 3 | 44 (aver. of 3 trials) |
| | 9.17 | 3 | 40 (aver. of 3 trials) |
| CH$_2$(OH)$_2$ [a] | 11.18 | 3 | 25 (aver. of 4 trials) |
| HCOOH | 10.89 | 3 | 9.3 (no Cl$^-$) |
| | 8.94 | 8.5 | 21 |

[a] For CH$_2$(OH)$_2$, some CH$_3$OH was present initially because they were added as a polymerization inhibitor in the concentrated formaldehyde bottle. $\Delta$[CH$_2$(OH)$_2$] was calculated by subtracting $\Delta$[CH$_3$OH] from $\Delta$[CH$_2$(OH)$_2$] in order to account for CH$_2$(OH)$_2$ generated from CH$_3$OH oxidation.

Possible explanations for the discrepancy between the rates. The rate constants derived from simulation and stoichiometric reactions outside the EMOR reactor are all apparent or observed rate constants ($k_{obs}$) which are extrinsic values that depend on the reaction conditions employed. While this precludes a direct comparison between the two sets of rate constants, comparison of the ratios of these rate constants, i.e. selectivities, can be made.

The comparison shows that the selectivity of $Pt^{II}$ for CH$_4$ over CH$_3$OH was similar ($k_1/k_2$=0.8-1.2 vs. 0.6 for EMOR-simulated vs. non-EMOR estimation), but rates of further oxidation of CH$_3$OH showed greater discrepancies ($k_2/k_3$=0.2 vs.>1 and $k_3/k_4$=0.2 vs>>1). These differences may point to $Pt^0$-catalyzed oxidation of CH$_2$(OH)$_2$ and HCOOH. While Cl-adsorption effectively suppresses the oxidation of CH$_3$OH, it is unknown whether it will be equally effective in suppressing the oxidation of CH$_2$(OH)$_2$ and HCOOH. This implies that the simulation-derived rate constants for $Pt^{II}$-catalyzed oxidation of CH$_2$(OH)$_2$ and HCOOH may have been overestimations.

Example 9. Control Experiment for Assessing Product Oxidation by $VO^{2+}$ in the Counter Compartment As explained earlier, methane oxidation products in the reactor freely migrate to other parts of the reactor such as the reference and counter compartments via vaporization. The counter compartment contained a high (3 M) concentration of vanadyl sulfate, which has an oxidation potential capable of oxidizing methanol. It is, therefore, important to estimate the degree of product oxidation, if any, that occurs due to the vanadyl ions. The reactor was set up in the usual way except that the working solution was blank electrolyte spiked with 4.6 mM of CH$_3$OH (total 105 µmol) without any Pt ions. The cell was pressurized with CH$_4$ as usual and heated at 130° C. for 37 hr. After 37 hr, 0.7 µmol of CH$_2$(OH)$_2$ and 2.5 µmol of CO$_2$ were recorded. This amounts to ~0.004 µmol of CH$_2$(OH)$_2$ and ~0.015 µmol of CO$_2$ from 1 mM of CH$_3$OH per hour. From this, it is estimated that ~2% of the total CH$_2$(OH)$_2$ and ~10% of the total CO$_2$ formed in the EMOR reactors may be attributed to oxidation by vanadyl ions in the counter compartment. As both CH$_2$(OH)$_2$ and CO$_2$ are minor products in the reactor trials, this contribution in the analysis was ignored.

Example 10. Faradaic Efficiency Measurements

Faradaic efficiency (FE) is defined by the mols of product of electron transfer divided by the mols of electrons that were passed through the circuit.

Bulk electrolysis of $Pt^{II}$ to $Pt^{IV}$ at 130° C. 22 or 23 mL solutions of 5 mM of K$_2$PtCl$_4$, 5 mM Na$_2$PtCl$_6$ and 10 mM NaCl in 0.5 M H$_2$SO$_4$ were oxidized with stirring at a Pt foil working electrode. A pure $Pt^{II}$ solution was not used because of its tendency towards disproportionation and $Pt^0$ precipitation at elevated temperatures. The [$Pt^{IV}$] at the end was measured by UV-Vis spectroscopy to calculate the µmol of $Pt^{IV}$ generated ($\Delta Pt^{IV}$). The [$Pt^{IV}$] at the end was measured by UV-Vis spectroscopy to calculate the µmol of $Pt^{IV}$ generated ($\Delta Pt^{IV}$) using the following equation: FE=2*$\Delta Pt^{IV}$/(µmol of e$^-$).

At the three different potentials that were tested, the Faradaic efficiencies were ~100%. See Table 1 for the results. That additional error arises from the difficulty of measuring the solution volume (reduced due to evaporation within the reactor) accurately after the reaction.

Faradaic efficiency of EMOR reactors. In the presence of methane, $Pt^{IV}$ in the solution is consumed by reacting with methane or products from methane oxidation. The overall Faradaic efficiency was calculated by summing up the µmols of the methane oxidation products multiplied by the number of oxidized equivalents according to FIG. 5, (b) and the change in the amount of $Pt^{IV}$ ions ($\Delta Pt^{IV}=Pt^{IV}_{final}-Pt^{IV}_{initial}$). In brief, $$FE=2*(n_{CH3OH}+n_{CH3Cl}+2*n_{CH2(OH)2}+3*n_{HCOOH}+4*n_{CO2}+\Delta Pt^{IV})/n_{e-}$$

where $n_i$ denotes the mols of species i. Solutions in the working compartment, in the reference electrode compartment, and droplets condensed on the inner surfaces of the reactor were separately collected and analyzed by NMR to determine the concentrations of CH$_3$OH, CH$_2$(OH)$_2$ and HCOOH. These were multiplied by the respective solution volumes, and combined. As noted above, NMR quantitation of the counter compartment solution could not be carried out due to the high concentration of paramagnetic vanadium species. The headspace gas was analyzed for CH$_3$Cl and CO$_2$ (vide supra). The result is shown in Table 3.

Because the FE for $Pt^{II}$ electro-oxidation is ~100%, the FE for the EMOR reactors should also be ~100%. Indeed, close to 100% FE values were observed. The missing FE may be accounted for by the products in the counter compartment that were not quantitated. Also, a significant margin of error is expected, as there are several sources of potential errors, e.g. NMR and GC measurements, solution volume estimation, possible deviation of gas solubility from that in pure water, etc.

Example 11. Quantitation of Pt Ions by UV-Vis Spectroscopy

Quantitation of the $Pt^{II}$ and $Pt^{IV}$ ions was performed with UV-vis spectroscopy (Cary 50, Agilent). $Pt^{IV}Cl_6^{2-}$ ions in aqueous solutions show a strong absorption at 262 nm, where $Pt^{II}Cl_4^{2-}$ ions absorb little.[5] $Pt^{II}Cl_4^{2-}$ ions show an absorption maximum at 214 nm, but this peak is often covered up under the broad absorbance of $Pt^{IV}Cl_6^{2-}$ in mixed solutions.* On the other hand, the total concentration of Pt ions could be determined by reaction with SnCl$_2$[43] which gives rise to a strong absorbance at 404 nm. Therefore, the concentration of $Pt^{II}$ and $Pt^{IV}$ was determined by measuring the absorbance at 262 nm and the total concentration using the following equation, where $\varepsilon_{PtIV}$ and $\varepsilon_{PtII}$ denote the extinction coefficients of $Pt^{II}$ and $Pt^{IV}$ at 262 nm, and d denotes the dilution factor:

$$[Pt^{IV}]=(A_{262\ nm}/d-\varepsilon_{PtV}*[Pt]_{total})/(\varepsilon_{PtIV}-\varepsilon_{PtII})$$

$$[Pt^{II}]=[Pt]_{total}-[Pt^{IV}]$$

Importantly, $Pt^{II}Cl_4^{2-}$ and $Pt^{IV}Cl_6^{2-}$ ions undergo hydrolysis over time, and the species with less $Cl^-$ coordination has different values of extinction coefficient. Therefore, each sample was diluted in 1 M HCl and irradiated with a 4W UV lamp (252 or 365 nm) for >5 min. for complete anation prior to measurement of the 262 nm absorbance.[44]

Figure 24:
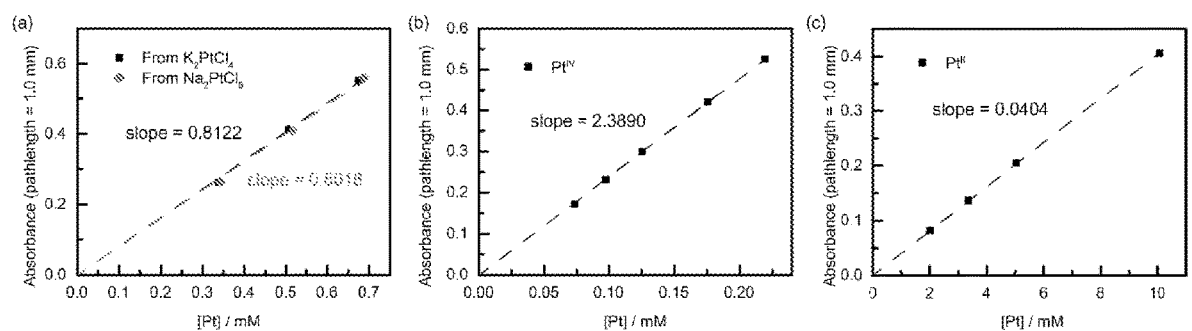
FIG. 24 depicts calibration curves for Pt ion quantitation by UV-vis.

Determination of ε for $[Pt^{II}]_{total}$. Both $Pt^{II}$ and $Pt^{IV}$ ($Pt^{IV}$ is reduced to $Pt^{II}$ prior to complexation) undergo complexation with $Sn^{II}Cl_3^-$ to give a strong orange-red color.[45] For accurate determination of the extinction coefficient at 404 nm, a Beer's plot was constructed with solutions of $Pt^{II}$ and $Pt^{IV}$ whose Pt concentrations were determined by ICP-MS. Stock solutions of $Pt^{II}$ and $Pt^{IV}$ were prepared from $K_2PtCl_4$ and $Na_2PtCl_6$, respectively. These stock solutions were diluted to three different concentrations with a 1 M $SnCl_2$+3 M HCl solution and reacted for >5 min. The background subtracted absorbance was then plotted against the concentration determined by ICP-MS to give the extinction coefficient (FIG. 24, (a)). The average value $8.069\times10^3$ cm$^{-1}$ M$^{-1}$ was taken as the extinction coefficient for determination of $[Pt]_{total}$.**

Determination of $\varepsilon_{PtIV}$ and $\varepsilon_{PtII}$ at 262 nm. Freshly prepared stock solutions of $K_2PtCl_4$ and $Na_2PtCl_6$ were serially diluted in 1 M HCl and measured (FIG. 24, (b), (c)). $\varepsilon_{PtIV}$=2.389×10$^4$ cm$^{-1}$ M$^{-1}$ and $\varepsilon^{PtII}$=4.04×10$^2$ cm$^{-1}$ M$^{-1}$.**

*Note I: During the course of the work, it was discovered that the second absorption maximum of $Pt^{II}Cl_4^{2-}$ ions at 230 nm, though lower in extinction coefficient (7.2×10$^3$ cm$^{-1}$ M$^{-1}$),[46] is suitable for determination of $[Pt^{II}]$ because absorption by $Pt^{IV}Cl_6^{2-}$ ions hits a minimum at this wavelength. An alternative quantitation protocol that uses the absorbance at 230 nm and 262 nm showed identical results to the protocol described above that uses absorbance at 262 nm and 404 nm from the $SnCl_3^-$ complex of Pt ions.

**Note II: The exact value of the extinction coefficients may slightly vary from the true values as the spectrometer was not calibrated with external standards (e.g. $\varepsilon_{PtIV}$ at 262 nm=2.45×10$^3$ M$^{-1}$ cm$^{-1}$ according to ref. 47). However, this does not compromise the validity of the results because the same spectrometer was used throughout the studies and linearity of response was confirmed in the absorbance range (A=0.1-0.7) where measurement was carried out.

Figure 25:
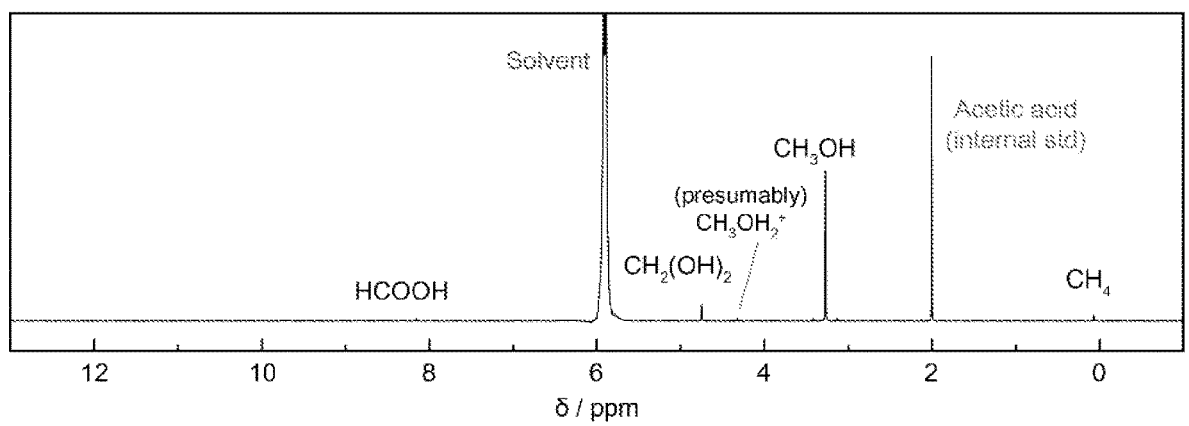
FIG. 25 depicts baseline-corrected (Whittaker smoother) spectrum of the working solution from an EMOR trial (entry 3 in Table 2). The wet pulse sequence was employed for solvent suppression. The spectrum is referenced to the acetic acid peak at 2.0 ppm.
Figure 26:
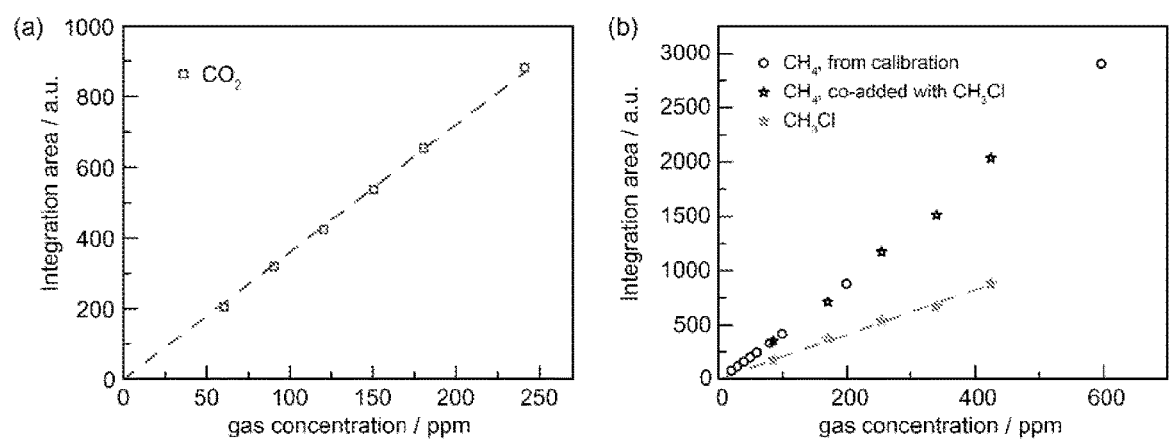
FIG. 26 depicts counter curves for quantitation by gas chromatography of (a) $CO_2$ and (b) $CH_3Cl$.

Example 12. Determination of Methane Oxidation Products $CH_3OH$, $CH_2(OH)_2$ and HCOOH. These solution-phase products were determined by NMR (Varian 500 MHz or Bruker 500/600 MHz instruments) with various solvent suppression techniques to suppress the $H_2O$ peak (presaturation, excitation sculpting or wet). The sample solution was mixed with 25 vol % of $D_2O$ solution containing acetic acid internal standard (caution: prolonged storage of this internal standard solution compromises the measured concentration via slow H/D exchange of $CH_3COOH$ in $D_2O$), then adjusted to ~2 M total acid concentration by the addition of 8 M $D_2SO_4$. This was done because the peak position of $CH_2(OH)_2$ (hydrated form of formaldehyde, which is the predominant form in 0.5 M $H_2SO_4$) was close to that of the solvent water; lowering the pH shifted the water peak more downfield and allowed us to observe and integrate the $CH_2(OH)_2$ peak (representative spectrum in FIG. 25). However, the high acid concentration made the NMR probe tuning less accurate and introduced systematic errors. Decreasing the sample size by using a 3 mm-dia. tube instead of 5 mm improved the tuning and the errors in integration areas. The 90°-pulse width was also manually calibrated for each sample. When only the concentration of $CH_3OH$ or HCOOH was of interest (e.g. during electrolyte optimization), addition of 8 M $D_2SO_4$ was omitted. The spectra were processed in MestReNova with phase and baseline correction. Integration was obtained by the sum method, as shimming was generally not very good because of the high H$^+$ concentration.

For determining methane oxidation products in the reactor, solutions were collected from the working compartment, reference compartment, and droplets condensed on the inner walls. All of them contained some product because the high temperature of the reactor causes product migration via vaporization. The extent of migration was greater with longer reactor operations. As for small amounts of products in the counter compartment (counter compartment volume (3 mL)<<working compartment volume (23 mL)), the high concentration of paramagnetic vanadyl ions precluded their determination by NMR and were therefore excluded.

$CO_2$ and $CH_3Cl$. These gaseous products were determined by gas chromatography (GC) measurement (SRI instruments, model 8610C) of the reactor headspace gas after the reactor has cooled down to room temperature. $CO_2$ was calibrated by serial dilution of a commercial calibration gas (Product no. X08AR98C33A0000, Airgas) with Ar (FIG. 27, (a)). $CH_3Cl$ was calibrated by diluting $CH_3Cl$ gas (Sigma Aldrich) in a septum-capped, air-filled 1 L flask along with equal amounts of $CH_4$, which was already calibrated as it was a component of the calibration gas (FIG. 27, (b)). In this way, systematic error was minimized. To account for the amount of $CO_2$ and $CH_3Cl$ dissolved in the solution phase, Henry's constants at room temperature were adopted from the NIST webbook (0.034 and 0.12 mol kg$^{-1}$ bar$^{-1}$ for $CO_2$ and $CH_3Cl$, respectively) to calculate the solution concentration of each gas from its partial pressure determined by GC.

Example 13. Estimation of Reaction Rates of $Pt^{II}$-Catalyzed C—H Oxidations In order to assess reaction rates of non-electrochemical catalysis by $Pt^{II}$ (i.e. $Pt^{IV}$ are stoichiometric oxidants and no re-oxidation of $Pt^{II}$ occurs), solutions of $Pt^{II}$+$Pt^{IV}$ were heated in the presence of substrate in heavy-walled NMR tubes or glass ampules.

To measure the rate of methane oxidation, heavy-walled NMR tubes (Norell, item no. S-5-500-HW-7) were charged with solutions of $Pt^{II}$ and $Pt^{IV}$, pressurized to 100 psi of methane, and manually agitated for >2 min. to allow gas-liquid mixing and dissolve methane. The tubes were placed in a stirred oil bath and heated to 130° C. After a set time (typically ~1.5 hr), the tubes were cooled down and the solution was withdrawn and analyzed by NMR.

To measure the oxidation rate of methanol, formaldehyde, and formic acid, solutions of $Pt^{II}$ and $Pt^{IV}$ containing the substrate were flame-sealed in scored glass ampules (Kimble Chase, 1 mL, item no. 12010L-1), placed in an aluminum heating block with silicone oil, and heated to 130° C.

Example 14. Reactor Configuration for Electrochemical Methane Oxidation in Flow A flow electrochemical reactor is an advantageous system, which can be utilized in electrochemical oxidation of methane in view of the presently disclosed process for maintaining catalytically active $Pt^{II}$ in the methane oxidation system over prolonged periods of time. The necessary aspects of the flow electrochemical reactor involve:

1) Efficient mass transport of methane and Pt ions;
2) Incorporation of a robust H$^+$-conducting membrane and appropriate counter reaction at the cathode; and
3) In situ separation of the product.

Figure 6:
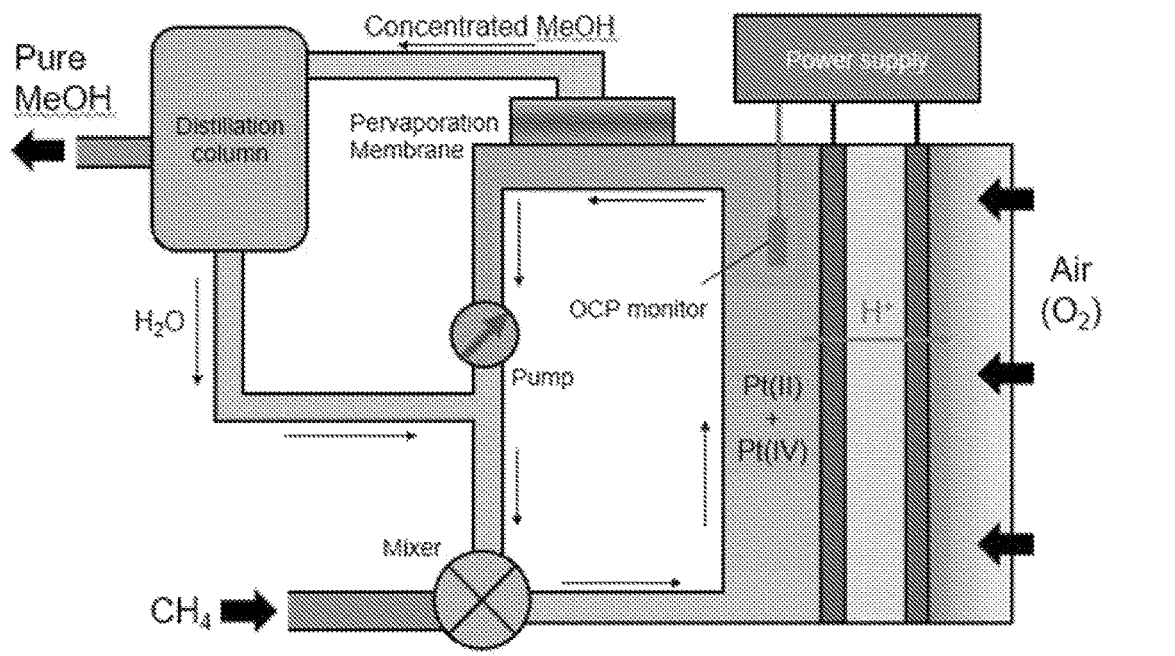
FIG. 6 depicts a schematic representation of an appropriate electrochemical flow reactor design.

A schematic representation of an appropriate electrochemical flow reactor design is shown in FIG. 6.

REFERENCES CITED (1) Da Silva, M. J. Synthesis of Methanol from Methane: Challenges and Advances on the Multi-Step (Syngas) and One-Step Routes (DMTM). *Fuel Process. Technol.* 2016, 145, 42-61.
(2) Wang, B.; Albarracín-Suazo, S.; Pagan-Torres, Y.; Nikolla, E. Advances in Methane Conversion Processes. *Catal. Today* 2017, 285, 147-158.
(3) Olah, G. A. Beyond Oil and Gas: The Methanol Economy. *Angew. Chemie Int. Ed.* 2005, 44 (18), 2636-2639.
(4) Holmen, A. Direct Conversion of Methane to Fuels and Chemicals. *Catal. Today* 2009, 142 (1-2), 2-8.
(5) Bank, W. Zero Routine Flaring by 2030 http://www.worldbank.org/en/programs/zero-routine-flaring-by-2030.
(6) Promoppatum, P.; Viswanathan, V. Identifying Material and Device Targets for a Flare Gas Recovery System Utilizing Electrochemical Conversion of Methane to Methanol. *ACS Sustain. Chem. Eng.* 2016, 4 (3), 1736-1745.
(7) Wogan, T. Methane to methanol catalyst could end gas flaring https://www.chemistryworld.com/news/methane-to-methanol-catalyst-could-end-gas-flaring/3007247.article.
(8) Ravi, M.; Ranocchiari, M.; van Bokhoven, J. A. The Direct Catalytic Oxidation of Methane to Methanol—A Critical Assessment. *Angew. Chemie—Int. Ed.* 2017, 56 (52), 16464-16483.
(9) Silva, M. J. Synthesis of Methanol from Methane: Challenges and Advances on the Multi-Step (Syngas) and One-Step Routes (DMTM). *Fuel Process. Technol.* 2016, 145, 42-61.
(10) Latimer, A. A.; Kakekhani, A.; Kulkarni, A. R.; Nørskov, J. K. Direct Methane to Methanol: The Selectivity-Conversion Limit and Design Strategies. *ACS Catal.* 2018, 8 (8), 6894-6907.
(11) Cui, X.; Li, H.; Wang, Y.; Hu, Y.; Hua, L.; Li, H.; Han, X.; Liu, Q.; Yang, F.; He, L.; et al. Room-Temperature Methane Conversion by Graphene-Confined Single Iron Atoms. *Chem* 2018, 4 (8), 1902-1910.
(12) Owen, J. S.; Labinger, J. A.; Bercaw, J. E. Kinetics and Mechanism of Methane, Methanol, and Dimethyl Ether C—H Activation with Electrophilic Platinum Complexes. *J. Am. Chem. Soc.* 2006, 128 (6), 2005-2016.
(13) Labinger, J. A. Chapter 2. Alkane Functionalization via Electrophilic Activation. In *Catalysis by Metal Complexes: vol. 38, Alkane C—H Activation by Single-Site Metal Catalysis;* Pérez, P. J., Ed.; Catalysis by Metal Complexes; Springer Netherlands: Dordrecht, 2012; Vol. 38, pp 17-71.
(14) Gunsalus, N. J.; Koppaka, A.; Park, S. H.; Bischof, S. M.; Hashiguchi, B. G.; Periana, R. A. Homogeneous Functionalization of Methane. *Chem. Rev.* 2017, 117 (13), 8521-8573.
(15) Labinger, J. A.; Bercaw, J. E. Mechanistic Studies on the Shilov System: A Retrospective. *J. Organomet. Chem.* 2015, 793, 47-53.
(16) DeVries, N.; Roe, D. C.; Thorn, D. L. Catalytic Hydroxylation Using Chloroplatinum Compounds. *J. Mol. Catal. A Chem.* 2002, 189 (1), 17-22.
(17) Weinberg, D. R.; Labinger, J. A.; Bercaw, J. E. Competitive Oxidation and Protonation of Aqueous Monomethylplatinum(II) Complexes: A Comparison of Oxidants. *Organometallics* 2007, 26 (1), 167-172.
(18) Lin, M.; Shen, C.; Garcia-zayas, E. A.; Park, U. V; Pennsyl, V.; June, R. V; Sen, A.; Park, U. V; Pennsyl, V.; June, R. V. Catalytic Shilov Chemistry: Platinum Chloride-Catalyzed Oxidation of Terminal Methyl Groups by Dioxygen. *J. Am. Chem. Soc.* 2001, 123 (5), 1000-1001.
(19) Bar-Nahum, I.; Khenkin, A. M.; Neumann, R. Mild, Aqueous, Aerobic, Catalytic Oxidation of Methane to Methanol and Acetaldehyde Catalyzed by a Supported Bipyrimidinylplatinum-Polyoxometalate Hybrid Compound. *J. Am. Chem. Soc.* 2004, 126 (33), 10236-10237.
(20) Kreutz, J. E.; Shukhaev, A.; Du, W.; Druskin, S.; Daugulis, O.; Ismagilov, R. F. Evolution of Catalysts Directed by Genetic Algorithms in a Plug-Based Microfluidic Device Tested with Oxidation of Methane by Oxygen. *J. Am. Chem. Soc.* 2010, 132 (9), 3128-3132.
(21) Lee, M.; Sanford, M. S. Platinum-Catalyzed, Terminal-Selective C(Sp3)-H Oxidation of Aliphatic Amines. *J. Am. Chem. Soc.* 2015, 137 (40), 12796-12799.
(22) Horváth, I. T.; Cook, R. A.; Millar, J. M.; Kiss, G. Low-Temperature Methane Chlorination with Aqueous Platinum Chlorides in the Presence of Chlorine. *Organometallics* 1993, 12 (1), 8-10.
(23) Liu, S. F.; Nusrat, F. Electrocatalytic Shilov Chemistry for the Oxidation of Aliphatic Groups. *Mol. Catal.* 2019, 463 (October 2018), 16-19.
(24) Freund, M. S.; Labinger, J. A.; Lewis, N. S.; Bercaw, J. E. Electrocatalytic Functionalization of Alkanes Using Aqueous Platinum Salts. *J. Mol. Catal.* 1994, 87 (1), L11-L15.
(25) Lappin, G. *Redox Mechanisms in Inorganic Chemistry*; Ellis Horwood: New York, 1994.
(26) Jude, H.; Krause Bauer, J. A.; Connick, W. B. An Outer-Sphere Two-Electron Platinum Reagent. *J. Am. Chem. Soc.* 2003, 125 (12), 3446-3447.
(27) O'Reilly, M. E.; Kim, R. S.; Oh, S.; Surendranath, Y.; O'Reilly, M. E.; Kim, R. S.; Oh, S.; Surendranath, Y. Catalytic Methane Monofunctionalization by an Electrogenerated High-Valent Pd Intermediate. *ACS Cent. Sci.* 2017, 3 (11), 1174-1179.
(28) Cushing, J. P.; Hubbard, A. T. Study of the Kinetics of Electrochemical Reactions By Thin Layer Voltammetry. II. Electro-Oxidation of Platinum (II) Complexes. *Electroanal. Chem. Interfacial Electrochem.* 1969, 23, 183-203.
(29) CRC Handbook. Handbook of Chemistry and Physics 99th Edition.
(30) Elding, L. I. Preparation and Properties of the Tetra-Aquaplatinum(II) Ion in Perchloric Acid Solution. *Inorganica Chim. Acta* 1976, 20, 65-69.
(31) Scortichini, C. L.; Reilley, C. N. Surface Characterization of Pt Electrodes Using Underpotential Deposition of H and Cu. V. Characterization of BD Pt Catalyst Surface. *J. Catal.* 1983, 79 (1), 138-146.
(32) Jerkiewicz, G.; Vatankhah, G.; Lessard, J.; Soriaga, M. P.; Park, Y. S. Surface-Oxide Growth at Platinum Electrodes in Aqueous H2SO 4 Reexamination of Its Mechanism through Combined Cyclic-Voltammetry, Electrochemical Quartz-Crystal Nanobalance, and Auger Electron Spectroscopy Measurements. *Electrochim. Acta* 2004, 49 (9-10), 1451-1459.

(33) Novak, D. M.; Conway, B. E. Competitive Adsorption and State of Charge of Halide Ions in Monolayer Oxide Film Growth Processes at Pt Anodes. *J. Chem. Soc. Faraday Trans. 1 Phys. Chem. Condens. Phases* 1981, 77 (10), 2341-2359.

(34) Compton, R. G.; Banks, C. E. *Understanding Voltammetry*, 2nd ed.; World Scientific Publishing: Singapore, 2007.

(35) Zhao, X.; Yin, M.; Ma, L.; Liang, L.; Liu, C.; Liao, J.; Lu, T.; Xing, W. Recent Advances in Catalysts for Direct Methanol Fuel Cells. *Energy Environ. Sci.* 2011, 4 (8), 2736.

(36) Chung, D. Y.; Lee, K. J.; Sung, Y. E. Methanol Electro-Oxidation on the Pt Surface: Revisiting the Cyclic Voltammetry Interpretation. *J. Phys. Chem. C* 2016, 120 (17), 9028-9035.

(37) Snell, K. D.; Keenan, A. G. Chloride Inhibition of Ethanol Electrooxidation at a Platinum Electrode in Aqueous Acid Solution. *Electrochim. Acta* 1981, 26 (9), 1339-1344.

(38) Sen, A.; Lin, M.; Kao, L. C.; Hutson, A. C. C—H Activation in Aqueous Medium. The Diverse Roles of Platinum(II) and Metallic Platinum in the Catalytic and Stoichiometric Oxidative Functionalization of Organic Substrates Including Alkanes. *J. Am. Chem. Soc.* 1992, 114 (16), 6385-6392.

(39) Cameron, R. E.; Bocarsly, A. B. Multielectron-Photoinduced Reduction of Chloroplatinum Complexes: Visible Light Deposition of Platinum Metal. *Inorg. Chem.* 1986, 25 (16), 2910-2913.

(40) Bratsch, S. G. Standard Electrode Potentials and Temperature Coefficients in Water at 298.15 K. *J. Phys. Chem. Ref Data* 1989, 18 (1), 1-21.

(41) Yadav, R.; Fedkiw, P. S. Analysis of EIS Technique and Nafion 117 Conductivity as a Function of Temperature and Relative Humidity. *J. Electrochem. Soc.* 2012, 159 (3), B340-B346.

(42) Kirkland, J. J.; Yoe, J. H. Ultraviolet Spectrophotometric Determination of Platinum. *Anal. Chim. Acta* 1953, 9, 441-445.

(43) Ayres, G. H.; Meyer, A. S. Spectrophotometric Study of the Platinum(IV)-Tin(II) Chloride System. *Anal. Chem.* 1951, 23 (2), 299-304.

(44) Elding, L. I.; Gustafson, L. Kinetics and Mechanism for Chloride Anation of Some Platinum(IV) Aqua Complexes in the Presence of Platinum(II). *Inorganica Chim. Acta* 1976, 19 (C), 31-38.

(45) Young, J. F.; Gillard, R. D.; Wilkinson, G. 992. Complexes of Ruthenium, Rhodium, Iridium, and Platinum with Tin(II) Chloride. *J. Chem. Soc.* 1964, 8 (5176), 5176.

(46) Elding, L. I. L. I.; Olsson, L. F. Electronic Absorption Spectra of Square-Planar Chloro-Aqua and Bromo-Aqua Complexes of Palladium(II) and Platinum(II). *J. Phys. Chem.* 1978, 82 (1), 69-74.

(47) Cox, L. E.; Peters, D. G.; Wehry, E. L. Photoaquation of Hexachloroplatinate(IV). *J. Inorg. Nucl. Chem.* 1972, 34 (1), 297-305.

(48) Xu, L.; Li, F.; Dong, S. Electro-Oxidation of a Chloride Complex of Platinum(II) at a Glassy Carbon Electrode. *J. Electroanal. Chem.* 1995, 383 (1-2), 133-137.

(49) Kent, C. A.; Concepcion, J. J.; Dares, C. J.; Torelli, D. A.; Rieth, A. J.; Miller, A. S.; Hoertz, P. G.; Meyer, T. J. Water Oxidation and Oxygen Monitoring by Cobalt-Modified Fluorine-Doped Tin Oxide Electrodes. *J. Am. Chem. Soc.* 2013, 135 (23), 8432-8435.

(50) Elding, L. I.; Gröning, A. B. The Solvent Path in Square-Planar Substitutions. Kinetics and Mechanism for Reactions of Tetrachloroplatinate(II) And Aquachloroplatinates(II) with Halides, Thiocyanate and Dimethyl Sulfoxide. *Inorganica Chim. Acta* 1978, 31 (C), 243-250.

(51) Shilov, A. E.; Shteinman, A. A. Activation of Saturated Hydrocarbons by Metal Complexes in Solutions. *Kinet. Catal.* 1977, 18 (5), 924-965.

(52) Ahlquist, M.; Nielsen, R. J.; Periana, R. A.; Goddard III, W. A. Product Protection, the Key to Developing High Performance Methane Selective Oxidation Catalysts. *J. Am. Chem. Soc.* 2009, 131 (47), 17110-17115.

(53) Siegbahn, P. E. M.; Crabtree, R. H. Modeling the Solvent Sphere: Mechanism of the Shilov Reaction. *J. Am. Chem. Soc.* 1996, 118 (18), 4442-4450.

(54) Shilov, A. E.; Shul'pin, G. B. *Activation and Catalytic Reactions of Saturated Hydrocarbons in the Presence of Metal Complexes*; Catalysis by Metal Complexes; Kluwer Academic Publishers: Dordrecht, 2002; Vol. 21.

(55) Gol'dshleger, N. F.; Shteinman, A. A. Pt(II) Complexes in Activation of Saturated Hydrocarbons. *React. Kinet. Catal. Lett.* 1977, 6 (1), 43-50.

(56) Henglein, A.; Ershov, B. G.; Malow, M. Absorption Spectrum and Some Chemical Reactions of Colloidal Platinum in Aqueous Solution. *J. Phys. Chem.* 1995, 99 (38), 14129-14136.

(57) Yaws, C. L. Yaws' Handbook of Thermodynamic and Physical Properties of Chemical Compounds https://app.knovel.com/web/toc.v/cid:kpYHTPPCC4/viewerType:toc/ (accessed Dec. 12, 2018).

(58) Balashova, N. A.; Kazarinov, V. E. Study of the Structure of the Electrical Double Layer on Platinum by the Radioactive Tracer Method. *Russ. Chem. Rev.* 1965, 34 (10), 730-736.

(59) Sen, A.; Benvenuto, M. A.; Lin, M.; Hutson, A. C.; Basickes, N. Activation of Methane and Ethane and Their Selective Oxidation to the Alcohols in Protic Media. *J. Am. Chem. Soc.* 1994, 116 (3), 998-1003.

INCORPORATION BY REFERENCE

All of the U.S. patents and U.S. patent application publications cited herein are hereby incorporated by reference. In case of conflict, the present specification, including definitions, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A process for oxidizing a compound, comprising:
   (i) providing a reaction mixture, comprising water, a $Pt^{II}$ species at an initial concentration, a compound of formula $R^1$-$R^2$, an anion, and a Bronsted acid;
   (ii) applying an electrical current to the reaction mixture at a temperature, thereby oxidizing the compound of formula $R^1$-$R^2$;
   (iii) measuring a reaction concentration of the $Pt^{II}$ species in the reaction mixture; and
   (iv) modulating the electrical current in situ to maintain the reaction concentration of the $Pt^{II}$ species during the process at about 95% to about 105% of the initial concentration;

wherein
the anion is chloride, fluoride, bromide, iodide, a carboxylate, nitrate, perchlorate, phosphate, or sulfate;
the initial concentration of $Pt^{II}$ species is about 1 mM to about 10 M;
$R^1$ is $C_1$-$C_{20}$ alkyl, $C_3$-$C_{12}$ cycloalkyl, $C_5$-$C_{10}$ heterocyclyl, $C_6$-$C_{12}$ aryl, or $C_5$-$C_{12}$ heteroaryl; and
$R^2$ is H, —OH, —C(=O)H, or —C(=O)OH.

2. The process claim 1, wherein the reaction mixture is contained within a reaction vessel comprising a working electrode, and a counter electrode, and, optionally, a reference electrode.

3. The process claim 2, wherein the reaction vessel further comprises a $Pt^{II}$ sensing electrode.

4. The process of claim 3, wherein the $Pt^{II}$ sensing electrode is selected from the group consisting of a Pt foil electrode, a Pt mesh electrode, a Pt wire electrode, and a platinized Pt/$H_2$ electrode.

5. The process of claim 2, wherein the reaction vessel is a flow reaction vessel.

6. The process of claim 2, wherein the working electrode is selected from the group consisting of a Pt foil electrode, a Pt mesh electrode, an Hg/$HgSO_4$ electrode, an Ag/AgCl electrode, a Pt wire electrode, a platinized Pt/$H_2$ electrode, a calomel electrode, a fluorine-doped tin oxide electrode, an indium-doped tin oxide electrode, a glassy carbon electrode, a carbon black electrode, a pyrolytic graphite electrode, a graphite electrode, a carbon nanotube electrode, and a boron-doped diamond electrode.

7. The process of claim 2, wherein the reference electrode is selected from the group consisting of a Pt foil electrode, a Pt mesh electrode, an Hg/$HgSO_4$ electrode, an Ag/AgCl electrode, a Pt wire electrode, a platinized Pt/$H_2$ electrode, a calomel electrode, a fluorine-doped tin oxide electrode, an indium-doped tin oxide electrode, a glassy carbon electrode, a carbon black electrode, a pyrolytic graphite electrode, a graphite electrode, a carbon nanotube electrode, and a boron-doped diamond electrode.

8. The process of claim 2, wherein the counter electrode is selected from the group consisting of a Pt foil electrode, a Pt mesh electrode, an Hg/$HgSO_4$ electrode, an Ag/AgCl electrode, a Pt wire electrode, a platinized Pt/$H_2$ electrode, a calomel electrode, a fluorine-doped tin oxide electrode, an indium-doped tin oxide electrode, a glassy carbon electrode, a carbon black electrode, a pyrolytic graphite electrode, a graphite electrode, a carbon nanotube electrode, and a boron-doped diamond electrode.

9. The process of claim 2, wherein the counter electrode is immersed in a solution of an electron acceptor.

10. The process of claim 9, wherein the electron acceptor is a proton or vanadyl sulfate.

11. The process of claim 2, wherein the counter electrode is an oxygen-consuming electrode.

12. The process of claim 1, wherein the reaction concentration of $Pt^{II}$ species is measured potentiometrically or with a $Pt^{II}$ sensing electrode.

13. The process of claim 1, wherein the anion is chloride, fluoride, a carboxylate, nitrate, perchlorate, phosphate, or sulfate, wherein the carboxylate is acetate.

14. The process of claim 1, wherein the $Pt^{II}$ species is selected from the group consisting of $K_2PtCl_4$, $Na_2PtCl_4$, $Li_2PtCl_4$, $H_2PtCl_4$, $(NH_4)_2PtCl_4$, $K_2PtBr_4$, $Na_2PtBr_4$, $Li_2PtBr_4$, $H_2PtBr_4$, $(NH_4)_2PtBr_4$, $K_2Pt(CN)_4$, $Na_2Pt(CN)I_4$, $Li_2Pt(CN)_4$, $H_2Pt(CN)_4$, $(NH_4)_2Pt(CN)_4$, $K_2PtCl_6$, $Na_2PtCl_6$, $Li_2PtCl_6$, $H_2PtCl_6$, $(NH_4)_2PtCl_6$, $Pt(NH_3)_4Cl_2$, $Pt(NH_3)_4(NO_3)_2$, $Pt(NH_3)_4(OH)_2$, $Pt(NH_3)_4Cl_4$, and $PtO_2$.

15. The process of claim 1, wherein the Bronsted acid is selected from the group consisting of $H_2SO_4$, HCl, $HNO_3$, $H_3PO_4$, $HClO_4$, and a carboxylic acid.

16. The process of claim 1, wherein the temperature is about 20° C. to about 500° C.

17. The process of claim 1, wherein the electrical current is applied at a constant current.

18. The process of claim 1, wherein the compound of formula $R^1$-$R^2$ is an alkane or a cycloalkane.

19. The process of claim 1, wherein the compound of formula $R^1$-$R^2$ is oxidized to an alcohol.

* * * * *